US011421978B2

(12) United States Patent
Kakuma

(10) Patent No.: US 11,421,978 B2
(45) Date of Patent: Aug. 23, 2022

(54) SCALABLE OPTICAL COHERENCE TOMOGRAPHY IMAGING DEVICE

(71) Applicant: THE YOSHIDA DENTAL MFG. CO., LTD., Tokyo (JP)

(72) Inventor: Hideo Kakuma, Tokyo (JP)

(73) Assignee: THE YOSHIDA DENTAL MFG. CO., LTD., Tokyo (JP)

( * ) Notice: Subject to any disclaimer, the term of this patent is extended or adjusted under 35 U.S.C. 154(b) by 138 days.

(21) Appl. No.: 16/594,004

(22) Filed: Oct. 5, 2019

(65) Prior Publication Data
US 2020/0113440 A1  Apr. 16, 2020

(30) Foreign Application Priority Data

Oct. 10, 2018 (JP) .............................. JP2018-192124

(51) Int. Cl.
*G01B 9/02091* (2022.01)
*A61B 5/00* (2006.01)
(Continued)

(52) U.S. Cl.
CPC ........ *G01B 9/02091* (2013.01); *A61B 5/0066* (2013.01); *A61B 5/0088* (2013.01); *A61C 9/0053* (2013.01); *G01N 21/4795* (2013.01)

(58) Field of Classification Search
CPC ..... A61B 5/0066; A61B 5/0088; A61B 3/102; A61B 5/0073; A61B 2090/3735;
(Continued)

(56) References Cited

U.S. PATENT DOCUMENTS

| 5,933,234 A * | 8/1999 | Lam .......................... G01J 3/42 356/309 |
| 6,259,835 B1 * | 7/2001 | Jing ..................... G02B 6/3514 385/16 |

(Continued)

FOREIGN PATENT DOCUMENTS

| JP | 2013233303 A | 11/2013 |
| JP | 2018521326 | 8/2018 |

OTHER PUBLICATIONS

Office Action, Japanese Patent Office, Japanese Patent Application No. 2018-192124, dated Sep. 8, 2020.

*Primary Examiner* — Michael P LaPage
(74) *Attorney, Agent, or Firm* — CRGO Global; Steven M. Greenberg

(57) ABSTRACT

An optical coherence tomography imaging device (OCT device) splits laser light emitted from a light source into measurement light for irradiating an object and reference light for irradiating a reference mirror, then analyze the interference light formed by combining scattered measurement light reflected back from the object and reflected reference light reflected from the reference mirror in order to generate tomographic images. An OCT device includes a probe, which is used for irradiating the object with measurement light and collecting scattered measurement light that is reflected back from the object, and an OCT main unit, which includes a light source for emitting measurement light. The probe is arranged on an odonto-therapy unit equipped with an instrument hanger, and includes a probe-connection optical fiber for transmitting measurement light and scattered measurement light. The probe-connection optical fiber is detachably connected to the OCT main unit.

7 Claims, 13 Drawing Sheets

(51) Int. Cl.
*G01N 21/47* (2006.01)
*A61C 9/00* (2006.01)
(58) Field of Classification Search
CPC ............ G01B 9/02091; G01B 9/02027; G01N 21/4795; A61C 9/0053
See application file for complete search history.

(56) References Cited

U.S. PATENT DOCUMENTS

| | | | |
|---|---|---|---|
| 7,181,102 B1* | 2/2007 | Fang | G02B 6/3514 |
| | | | 385/15 |
| 2009/0051228 A1* | 2/2009 | Kanbara | H02K 33/16 |
| | | | 310/14 |
| 2010/0290059 A1* | 11/2010 | Inoue | G01B 9/0205 |
| | | | 356/477 |
| 2012/0229812 A1* | 9/2012 | Liu | G01B 9/02069 |
| | | | 356/477 |
| 2015/0124261 A1* | 5/2015 | Jaillon | G01B 9/02091 |
| | | | 356/479 |
| 2015/0241202 A1* | 8/2015 | Jiang | G01B 9/02083 |
| | | | 356/479 |
| 2016/0045106 A1* | 2/2016 | Jaillon | G01B 9/02027 |
| | | | 351/221 |
| 2017/0023350 A1* | 1/2017 | Margallo | G01B 9/0207 |
| 2019/0056214 A1* | 2/2019 | Everett | A61B 3/152 |
| 2019/0078870 A1* | 3/2019 | Engel | G01B 9/02061 |
| 2019/0137253 A1* | 5/2019 | Trenholm | G01B 9/02091 |

* cited by examiner

SCALABLE OPTICAL COHERENCE TOMOGRAPHY IMAGING DEVICE

The present application claims priority under 35 U. S. C. § 119 to Japanese Patent Application No. 2018-192124, filed Oct. 10, 2018. The contents of this application are incorporated herein by reference in their entirety.

TECHNICAL FIELD

The invention is related to an optical coherence tomography imaging device for taking tomographic images of the interior of objects by utilizing the coherence of light.

BACKGROUND ART

Conventionally, an optical coherence tomography imaging device (an OCT device) for dentistry uses laser light emitted from a light source that is split into measurement light and reference light, so that the measurement light can be shone onto oral tissues and the reference light onto a reference mirror. The OCT device collects scattered measurement light that is reflected from the oral tissues using a probe, then combines this scattered measurement light with reflected reference light from the reference mirror using an optical multiplexer. By analyzing the interference patterns of the combined light (henceforth the "interference light"), tomographic images are generated by the OCT device.

The OCT device (a dental measurement apparatus) of Patent Document 1 (Japanese Unexamined Patent Application Publication No. 2013-233303) includes a probe for irradiating an object with measurement light and receiving the light that is reflected back, as well as a light source and an optical multiplexer as described above, and is composed of two primary components, namely an OCT main unit for generating tomographic images and a display device that may be arranged on the OCT main unit.

SUMMARY OF INVENTION

However, because the OCT device described in Patent Document 1 is configured from a single probe and a single OCT main unit to which this probe is connected, to install two probes, it becomes necessary to install two OCT main units to be in alignment with the number of probes. The increase in the number of OCT main units that must accompany the increase in the number of probes not only means that more space gets taken up, but that the incurred cost rises with the increase in the number of OCT main units.

The present invention is intended to provide an OCT device that is capable of accommodating an increase in the number of probes with a single OCT main unit.

To solve the problems mentioned above, an OCT device according to the present invention is a device that splits laser light emitted from a light source into measurement light for irradiating an object and reference light for irradiating a reference mirror, combines scattered measurement light reflected from the object and reflected reference light reflected from the reference mirror to create interference light, and generates an optical coherence tomography image (an OCT image) by analyzing the interference light. The OCT device comprises one or more probes for irradiating an object with the measurement light and collecting the scattered measurement light reflected from the object, one or more optical fibers for transmitting the measurement light to a probe and the scattered measurement light from the probe (henceforth a "probe-connection optical fiber"), and an OCT main unit that includes a light source necessary for emitting the measurement light, and an optical distributor for directing the laser light emitted from the light source to one of a plurality of the probes.

The present invention provides an OCT device that can accommodate an increase in the number of probes with a single OCT main unit.

DETAILED DESCRIPTION OF AN EMBODIMENT

A description of an OCT device 1 according to an embodiment of the present invention will be given in detail with reference to FIGS. 1 to 5.

OCT Device

Figure 1:
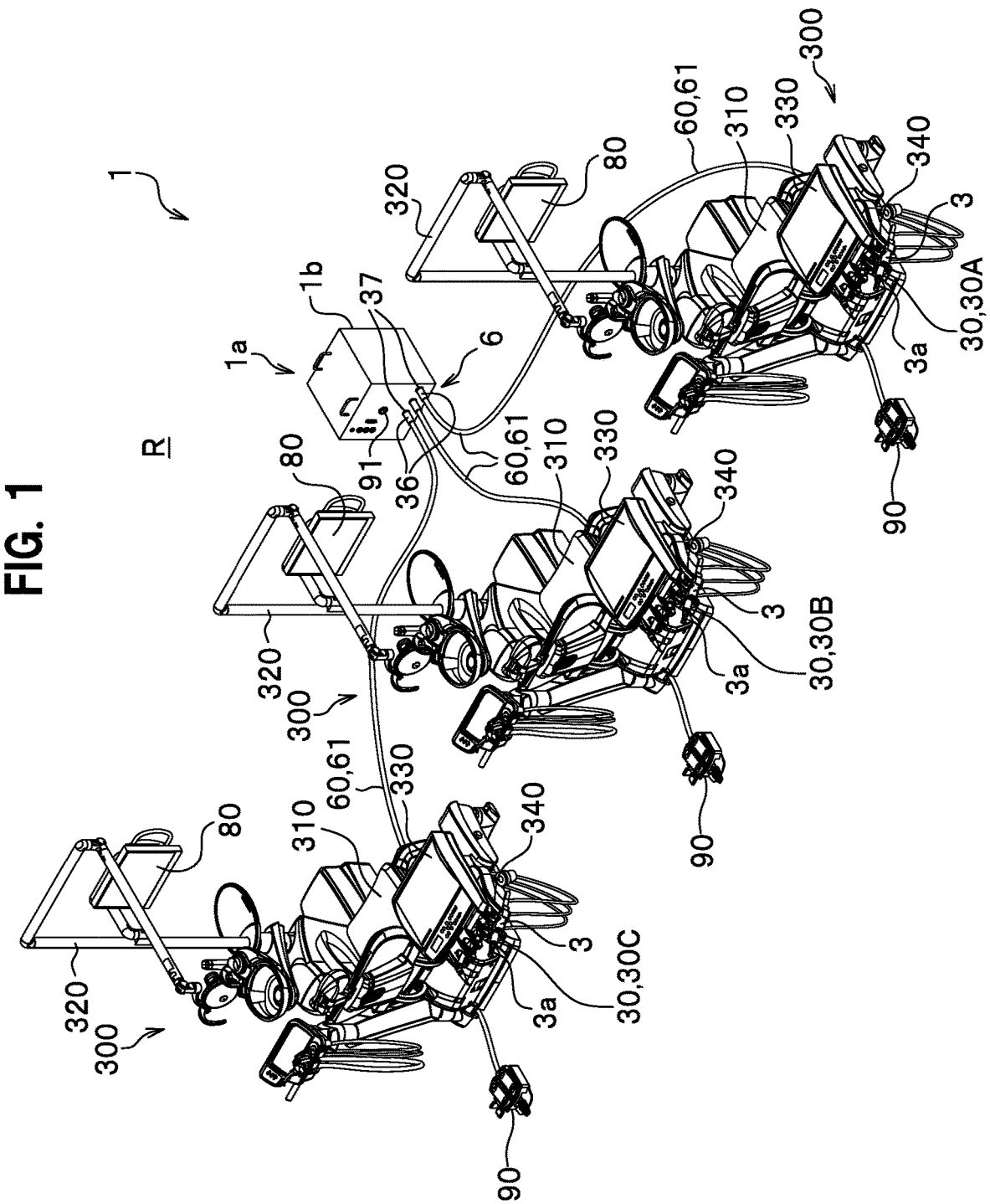
FIG. 1 is an external view of an example of an OCT device according to an embodiment of the present invention.

As shown in FIG. 1, the OCT device 1 is an image pickup device for taking tomographic images of a patient's tooth, a sample S (see FIG. 3), that is being diagnosed (the sample S may, for example, be a patient's front tooth). The OCT device 1 comprises a single OCT main unit 1a with an optical distributor 4, and, arranged separately for every odonto-therapy unit 300, a diagnostic probe part 30 (probe), a probe-connection optical fiber 61, a display device 80, an input device 9 (see FIG. 3), and a foot controller 90.

Note that the OCT device 1 will be explained using an example where the diagnostic probe part 30, the display device 80, the input device 9 (see FIG. 3), and the foot controller 90 are arranged on each of the three odontotherapy units 300 installed in an examination room R.

Figure 3:
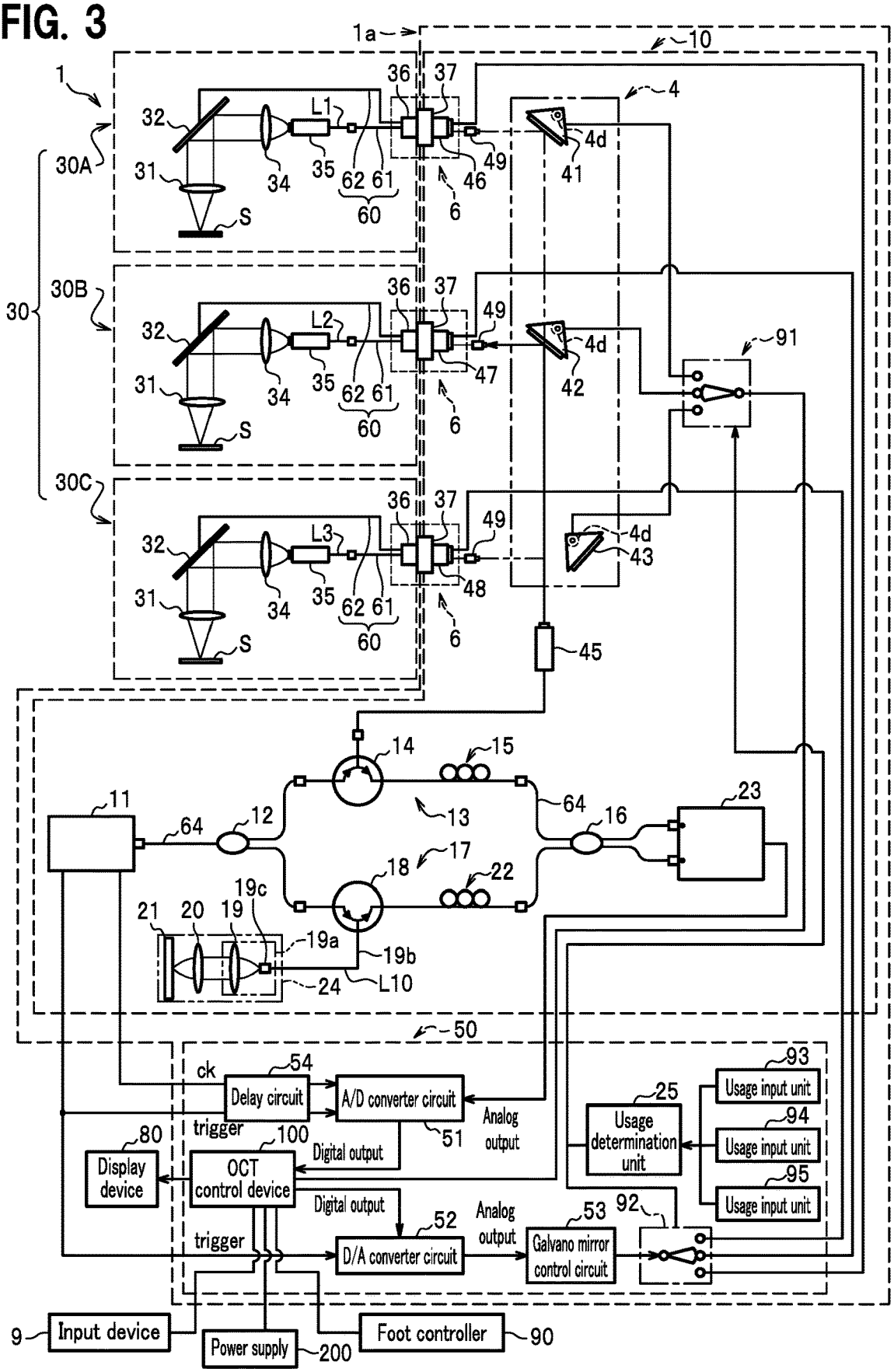
FIG. 3 is a block diagram of an example of an OCT device according to an embodiment of the present invention.

The OCT device 1 of FIG. 3 splits laser light emitted by a light source 11 into measurement light, used for irradiating a sample S, and reference light, used for irradiating a reference mirror 21. The diagnostic probe part 30 irradiates the sample S with this measurement light and collects scattered measurement light that is reflected from the sample S. By combining the scattered measurement light with the reflected reference light from the reference mirror 21 to form interference light and analyzing the interference light, the OCT device 1 generates an OCT image.

OCT Main Unit

The OCT main unit 1a primarily comprises a light source 11, an optical unit part 10 (an optical unit), a control unit part 50 (a control unit), a housing unit 1b (see FIG. 1), an optical distributor 4 arranged within the housing unit 1b, connectors 46, 47, and 48 arranged on the housing unit 1b, one or more fiber collimators 49, a usage switching unit 91, and a usage determination unit 25.

The housing unit 1b is a casing that encases components such as the optical unit part 10 and the control unit part 50.

Optical Distributor

As shown in FIG. 3, the optical distributor 4 is for directing laser light emitted by the light source 11 to one of a plurality of diagnostic probe parts 30 (diagnostic probe parts 30A-30C), and reflects laser light towards a connector plug 36 provided on each of the diagnostic probe parts 30A-30C. The optical distributor 4 is configured from one or more reflectors. For example, the optical distributor 4 in FIG. 3 is configured from three reflectors 41-43, in alignment with the three diagnostic probe parts 30A-30C.

Figure 5A:
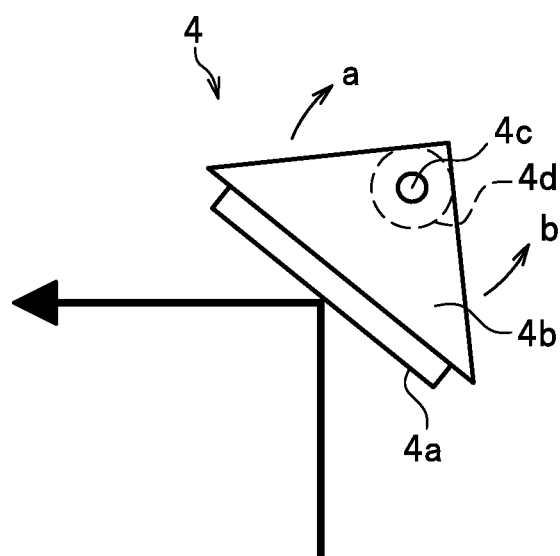
FIG. 5A is an enlarged side view of the principal part of an optical distributor configured from a reflector with a reflecting mirror.
Figure 5B:
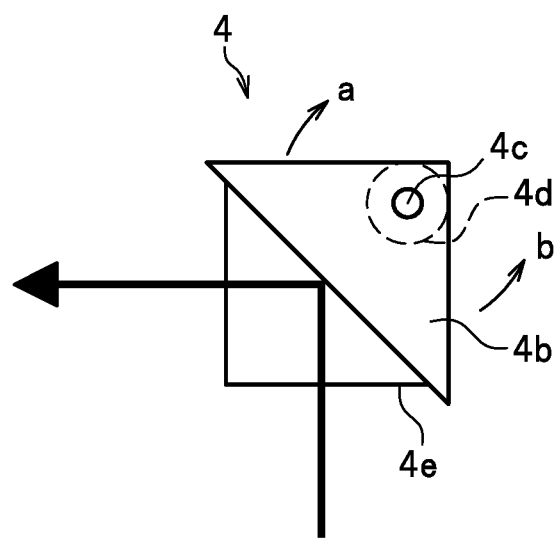
FIG. 5B is an enlarged side view of the principal part of an optical distributor configured from a reflector with a prism.

As shown in FIGS. 5A, 5B, the reflector of an optical distributor 4 comprises a reflector unit (either a reflecting mirror 4a or a prism 4e), a reflector support unit (a mirror mount 4b), a pivot 4c, and an actuator 4d.

The reflector unit is a member for reflecting laser light, and is in the form of a reflecting mirror 4a or a prism 4e. As shown in FIG. 5A, the reflecting mirror 4a is made of a mirror plate that reflects laser light coming from the light source 11 via a measurement-light-side circulator 14 onto a fiber collimator 49 that is arranged in front of each of the connectors 46-48. As shown in FIG. 5B, the prism 4e is, just like the reflecting mirror 4a, a member for reflecting laser light coming from the light source 11 via the measurement-light-side circulator 14 onto a fiber collimator 49 for a diagnostic probe part 30A, 30B, or 30C, and is made from a light guide (a transparent member) that is triangular in side view.

As shown in FIGS. 5A, 5B, the mirror mount 4b is a support for supporting the reflector unit (a reflecting mirror 4a or a prism 4e).

The actuator 4d is a switching device to enable the reflector unit to switch between a state where it can reflect laser light and a state where it does not receive laser light. In other words, the actuator 4d is a drive unit for rotating the reflecting mirror 4a by rotatably driving the pivot 4c so that laser light is directed towards the fiber collimator 49 for the diagnostic probe part 30A, 30B, or 30C. The actuator 4d may be of any kind, as long as it sets the angle of the reflecting mirror 4a to predefined angles, and is made from a rotation mechanism such as a servo motor, pulse motor, or DC motor. The switching of the actuators 4d of the three reflectors 41-43 in order to direct laser light to the diagnostic probe part 30 to be used is carried out with a usage switching unit 91.

The pivot 4c is a pivot member for rotatably supporting the mirror mount 4b.

Regarding the reflecting mirror 4a of the reflector unit, the surface of the mirror mount 4b can be used to reflect the laser light by giving the surface of the mirror mount 4b (the light reflecting side) a mirror finish.

Further, the reflecting mirror 4a of the reflector unit may, in addition to a mirror finish, be coated with a material having a high reflection coefficient in order to raise the reflection coefficient of the surface of the mirror mount 4b (the light reflecting side).

In other words, the reflector unit can be integrated with a reflector support unit (mirror mount 4b) if it is given a mirror finish with or without a coating over the mirror finish.

In this way, the reflecting mirror 4a of the reflector unit can be of any kind as long as it reflects laser light, and can be modified accordingly.

Figure 4:
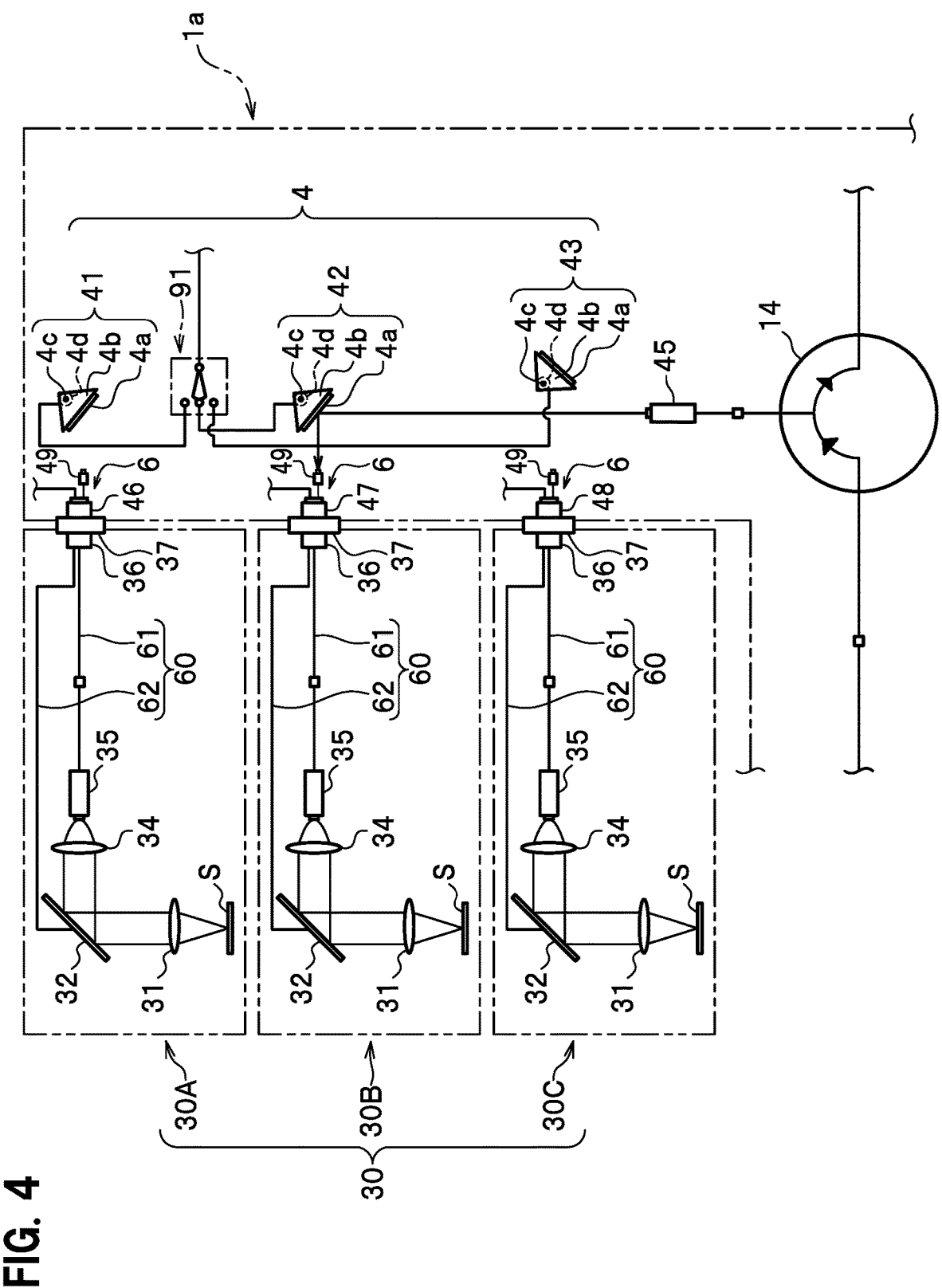
FIG. 4 is a block diagram of an example of an optical distributor.

As shown in FIG. 4, the reflectors 41-43 are arranged at appropriate intervals along the optical axis of the laser light from the fiber collimator 45. When the usage input units 93, 94, and 95 are switched off, the reflectors 41-43 are rotated, by the usage switching unit 91, so that the laser light from the fiber collimator 45 does not shine on the reflecting mirror 4a. Note that the reflector 41 that is positioned the furthest from the fiber collimator 45 may, when the usage input units 93-95 are switched off, have its reflecting mirror 4a at an angle for reflecting laser light from the fiber collimator 45 towards the fiber collimator 49 placed in front of the diagnostic probe part 30A. When a usage input unit 93, 94, or 95 is turned on, the actuator 4d of the corresponding reflector 41, 42, or 43 gets actuated by the usage switching unit 91 and rotates around the pivot 4c thereof, thereby making the reflecting mirror 4a thereof tilt at an angle that reflects the laser light from the fiber collimator 45 to the fiber collimator 49 of the corresponding diagnostic probe part 30.

Connectors

Connectors 46-48 are connecting instruments to which the connector plug 36 of a diagnostic probe part 30 is connected. For instance, a plurality of connectors 46-48 (say, three) are arranged on the side wall of a housing unit 1b. Connections between the connectors 46-48 and connector plugs 36 are held together by receptacles 37. On the inner side of the OCT main body 1a, the connectors 46-48 are each connected via an optical fiber 61 to a fiber collimator 49. Also, electrical wiring 62 coming out from the connectors 46-48 is connected to a galvano mirror control circuit 53 via the usage switching unit 92.

Optical Unit Part

The optical unit part 10 comprises a light source 11 that is suitable for general forms of optical coherence tomography, an optical system, and a detection part. The optical unit part 10 includes a light source 11 that irradiates a sample S with laser light using wavelengths swept over a broad spectral range, a coupler 12 (an optical splitter) that splits the laser light into measurement light irradiated on the sample S and reference light irradiated on the reference mirror 21, a coupler 16 that generates interference light by combining reflected reference light that is reference light reflected back from the reference mirror 21 and the scattered measurement light, a detector 23 that detects information regarding the interior of the sample S from the interference light, optical fibers 64 that form optical paths between the light source 11 and the detector 23, and other optical components.

Light emitted from the light source 11 is split into measurement light and reference light by the coupler 12 that works as an optical splitter. The measurement light is transmitted to any one of the diagnostic probe parts 30 via a measurement-light-side circulator 14 of the sample arm 13, the fiber collimator 45, an optical distributor 4, a fiber collimator 49, a connector 46, 47, or 48, and a connector plug 36. The measurement light travels via a receiver lens 34 (a collimator lens) and a scanning unit 32 (a galvano mirror) and is focused onto the sample S using a scanning-beam condenser lens 31. There, the measurement light is scattered and reflected back, and returns through the scanning-beam condenser lens 31, the scanning unit 32, the receiver lens 34, the fiber collimator 35, the connector plug 36, the connector 46, 47, or 48, the fiber collimator 49, the optical distributor 4, and the fiber collimator 45 to the measurement-light-side circulator 14 of the sample arm 13. The polarized component of the returning measurement light is returned to a state having less polarization by the use of a polarization controller 15, and is inputted to the detector 23 via the coupler 16 working as an optical multiplexer.

The reference light that is separated by the coupler 12 working as an optical splitter, on the other hand, passes through a reference-light-side circulator 18 of the reference arm 17, a collimator lens 19, and an optical-path-length alteration unit 24 (an optical-path-length setting unit) to be focused onto the reference mirror 21 by the reference-light condenser lens 20. The reference light is reflected by the reference mirror 21 and returns through the reference-light condenser lens 20 and the collimator lens 19 to the reference-light-side circulator 18. The polarized component of the returning reference light is returned to a state with little polarization by a polarization controller 22, then inputted to the detector 23 via the coupler 16 working as an optical multiplexer. Thus, the coupler 16 combines the measurement light that is scattered and reflected back by the sample S and reflected reference light that is reflected back by the reference mirror 21 so as to enable the detector 23 to detect the interference pattern of combined light (interference light) as information of the interior of the sample S.

As shown in FIG. 3, the reference-light-side optical-path-length alteration unit 24 is a device for altering the optical path length between the coupler 12 and the reference mirror 21 as well as for setting the original optical path length by moving the collimator lens 19 along the direction of an optical axis. The reference-light-side optical-path-length alteration unit 24 comprises, for example, a collimator lens unit (not shown in the figure) that holds the collimator lens 19 and is arranged so that it is capable of being driven electrically, together with the collimator lens 19, backwards and forwards along the optical axis through such means as an optical-path-length adjustment actuator, a reference-light condenser lens 20, a reference mirror 21, and a support frame member (not shown in the figure) that supports the collimator lens unit, the reference-light condenser lens 20, and the reference mirror 21.

The light source 11 may, for example, be a laser light source for an SS-OCT.

The reference-light-side collimator lens 19 is a lens used to converge the reference light, which was split by the coupler 12 (the optical splitter), into parallel light, and is encased in a substantially cylindrical lens holder (not shown in the figure) of a collimator 19a.

The collimator 19a comprises a collimator lens 19, a substantially cylindrical lens holder (not shown in figure) fitted with said collimator lens 19, a connector 19c that is located inside the lens holder (not shown in figure), a reference-light-side optical fiber 19b that is connected on one end to the connector 19c and on the other end to the reference-light-side circulator 18.

The reference-light condenser lens 20 is a lens for focusing parallel light converged by the collimator lens 19 onto the reference mirror 21.

Odonto-Therapy Unit

As mentioned before, the examination room R shown in FIG. 1 is installed with three odonto-therapy units 300 and one OCT main unit 1a. Each odonto-therapy unit 300 is arranged with a display device 80 that is connected individually to the OCT main unit 1a, a foot controller 90 that is connected individually to the OCT main unit 1a, and a diagnostic probe part 30 that is connected individually to the OCT main unit 1a. Each odonto-therapy unit 300 includes, for example, a dental chair 310, a display device 80, a support column with an arm 320, a dental table 330, and an instrument hanger 340 where the diagnostic probe part 30 is placed.

An input device 9 (see FIG. 3) is a controller that activates and terminates the optical-path-length adjustment actuator (not shown in figure) by instructing an actuator control part (not shown in figure) to alter the optical path length between the coupler 12 (an optical splitter) and the reference mirror 21. With the input device 9, it is possible to carry out operations including a switch operation by accessing the graphical user interface shown on the display device 80, such as by moving a slider with a cursor or selecting an icon with a pointer.

Further, the input device 9 includes a forward switch function for moving the collimator 19a forward by using the forward motion of the optical-path-length adjustment actuator (not shown in figure), and a reverse switch function for moving the collimator 19a backward by using the reverse motion of the optical-path-length adjustment actuator (not shown in figure).

The input device 9 may, for example, be a push switch 351 (se FIG. 2) located on the control panel 350 of the dental work table 330.

Figure 2:
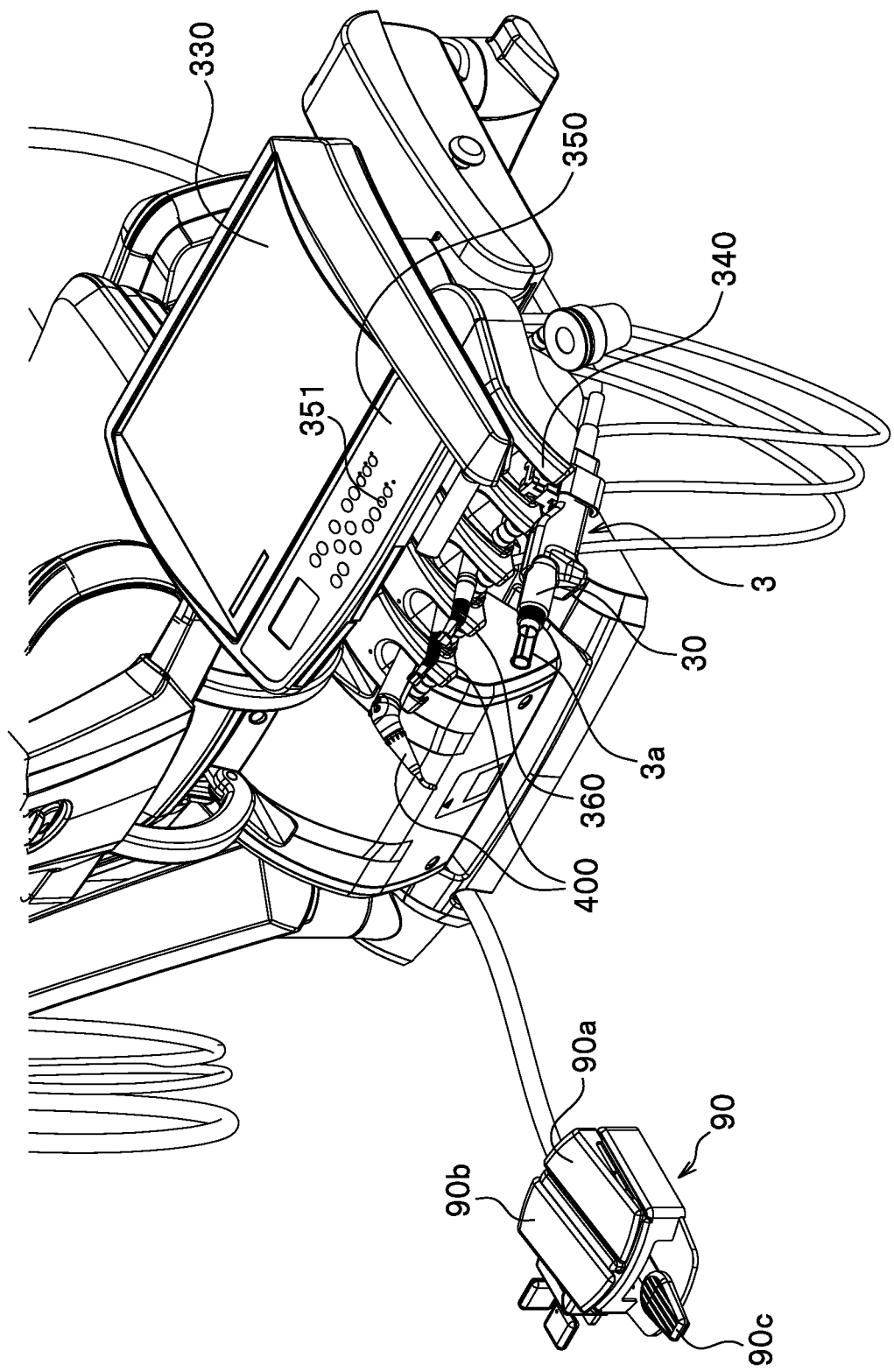
FIG. 2 is an enlarged perspective view of the principal part of an odonto-therapy unit shown in FIG. 1.

The foot controller 90 shown in FIG. 2 is composed of a foot pedal switch. The foot controller 90 is, for example, equipped with a control knob 90a to start capturing images, a control knob 90b to stop capturing images, and a control knob 90c to save an images that is taken, and is operable by foot. The foot controller 90 is communicably connected to the control unit portion 50 either by wire or a wireless means, so that a practitioner may operate the control button (not shown in figure) to begin taking images even when both of the practitioner's hands are full from handling a diagnostic probe part 30 and so on.

Usage Input Unit

As shown in FIG. 3, the usage input units 93-95 are switches to drive the actuators 4d. The usage input units 93-95 are used to switch between the reflectors 41-43 via the usage determination unit 25 and the usage switching unit 91 so that laser light emitted from the light source 11 is transmitted to a particular diagnostic probe part 30 that needs to be activated out of a plurality of diagnostic probe parts 30A-30C. The usage input units 93-95 also act as switches to supply power from the power supply 200 to that particular diagnostic probe part 30.

Note that the configuration, form, and installed location of the usage input units 93-95 are not particularly limited. For example, the usage input units 93-95 comprise a mechanical switch such as a rotary switch on the OCT main unit 1a, switches on hanger sensors, placement/displacement switches that switch on and off according to the placement and displacement of the diagnostic probe parts 30A-30C on and from the instrument hanger 340 of the odonto-therapy unit 300, on-off switches arranged on the diagnostic probe parts 30A-30C, and collectively refers to these switches.

Usage Determination Unit

The usage determination unit 25 determines whether a diagnostic probe part 30 may be used or not, based on the signals from the usage input units 93-95. For example, in the case where the diagnostic probe parts 30A-30C are provided with the usage input units 93-95 in the form of on-off switches, when the switch on one of the diagnostic probe parts, say, 30A, is switched on, the usage determination unit 25 determines whether the diagnostic probe part 30A can be used, not allowing the use thereof if another diagnostic probe part 30B or 30C is already in use. If none of the other diagnostic probe parts 30B and 30C are in use, the diagnostic probe part 30A can be used.

Usage Switching Unit

The usage switching unit 91 is a switching unit for enabling the use of a single diagnostic probe part 30 out of a plurality of diagnostic probe parts 30A-30C.

The usage switching unit 91 is a device for automatically switching components such as the reflector unit so that electric signals from the galvano mirror control circuit 53 and the measurement light reach the diagnostic probe part 30, based on the usage of the diagnostic probe parts 30A-30C as determined by the usage determination unit 25, which determines the use of a diagnostic probe part 30 out of a plurality of diagnostic probe parts 30A-30C.

Diagnostic Probe Part

The diagnostic probe part 30 (the probe) shown in FIG. 2 includes a scanning unit 32 (galvano mirror) that performs two-dimensional scans using laser light, and, in addition to guiding the laser light from the optical unit part 10 to a sample S, irradiates the sample S with the measurement light and collects the scattered measurement light reflected from the sample S to be guided to the optical unit part 10.

As shown in FIG. 1, the diagnostic probe parts 30, for example, consist of three diagnostic probe parts 30A-30C that are each arranged on the three odonto-therapy units installed in an examination room R. Each of the diagnostic probe parts 30A-30C comprises a connector plug 36 with a receptacle 37, a cable 60 (a probe-connection optical fiber 61), a housing 3, a frame (not shown in figure), a fiber collimator 35, a receiver lens 34, a scanning unit 32, a scanning-beam condenser lens 31, and a nozzle 3a (see FIG. 2).

As shown in FIG. 1, the housing 3 is a casing that encases the components of each of the diagnostic probe parts 30A-30C. The housing 3 is, for example, straight in shape in both a planar and side view. As shown in FIG. 3, the main components within the housing 3 are the frame (not shown in figure), the fiber collimator 35, the receiver lens 34, the scanning unit 32, and the scanning-beam condenser lens 31. Also, the cable 60 is arranged so that it protrudes from the housing 3.

The receiver lens 34 is a lens for adjusting the laser light diameter upon receiving the measurement light sent from the coupler 12 via the measurement-light-side circulator 14. A collimator lens, for example, may be used as a receiver lens.

The fiber collimator 35 is, for example, an integrated type that incorporates the receiver lens 34 (a collimator lens).

The scanning unit 32 is a mirror for changing the direction of the laser light coming from the receiver lens 34, and comprises an x-direction galvano mirror and a y-direction galvano mirror. The scanning unit 32 may be a two-dimensional micro-electro-mechanical systems mirror (a 2-D MEMS mirror) for a two-dimensional scan using laser light.

The scanning-beam condenser lens 31 is, as shown in FIG. 3, a lens for concentrating the scanning light beam of the scanning unit 32 and focusing the measurement light onto the sample S. Between the scanning-beam condenser lens 31 and the nozzle 3a, there is an optical convergence point adjusting device (not shown in figure) for adjusting the distance between the sample S abutted by the nozzle 3a and the scanning-beam condenser lens 31.

The nozzle 3a of FIG. 1 is a nozzle for front teeth, and has a cylindrical body with an opening at its tip. The opening is arranged in front of the scanning-beam condenser lens 31 (see FIG. 3) so that the measurement light can be irradiated on the sample S (see FIG. 3) and the scattered measurement light can be collected through it. The nozzle 3a is equipped with a nozzle extension mechanism (not shown in figure) that is capable of adjusting the distance between the scanning-beam condenser lens 31 (see FIG. 3) and the sample S (see FIG. 3) by advancing and retreating the tip with respect to the housing 3.

Cable

As shown in FIG. 1, the cable 60 is used to optically and electrically connect diagnostic probe parts 30 (individual diagnostic probe parts 30A-30C) with the OCT main unit 1a (the optical unit part 10 and the control unit part 50). The cable 60 incorporates, for example, a probe-connection optical fiber 61 that is connected to the optical unit part 10 (see FIG. 3) and electrical wiring 62 that is connected to the control unit part 50 (see FIG. 3). The cable 60 on the side of each diagnostic probe part 30 and the cable 60 on the side of the OCT main unit 1a are detachably connected together by a connection part 6.

As shown in FIG. 3, the probe-connection optical fiber 61 is a linear optical guide for transmitting the measurement light and the scattered measurement light to and from a diagnostic probe part 30. The electrical wiring 62 includes the wiring used to supply electricity from the power supply 200 to the scanning unit 32 via the OCT control device 100, the usage switching unit 91, and the connection part 6. Each set of the probe-connection optical fiber 61 and the electrical wiring 62 is detachably attached on one end to each of the connectors 46-48 on the OCT main unit 1a, and on the other end to each of the respective diagnostic probe parts 30A-30C.

Within the OCT device 1 having the optical distributor 4, the fiber lengths on the measurement light side that run from the measurement-light-side circulator 14 to each of the fiber collimators 35 corresponding to the diagnostic probe parts 30A, 30B, 30C (the lengths L1, L2, L3 of the probe-connection optical fibers 61) and the length of the reference-light-side optical fiber 19b (length L10) that runs from the reference-light-side circulator 18 to the collimator 19a are all equal in length. The lengths of the probe-connection optical fibers 61 on the measurement light side (the lengths L1, L2, L3) are, say, aligned to the length of the probe-connection optical fiber 61 for a diagnostic probe part 30 with the longest distance from the measurement-light-side circulator 14. The lengths L1, L2, L3 of the probe-connection optical fibers 61, running between the measurement-light-side circulator 14 and the fiber collimators 35 of each of the diagnostic probe parts 30A, 30B, 30C, and the length L10 of the reference-light-side optical fiber 19b, running between the reference-light-side circulator 18 and the collimator 19a are, say, 10 m.

Note that a probe-connection optical fiber 61 and electrical wiring 62 may be placed in a single tube as shown in FIG. 1, or, alternatively, wired separately.

Connection Part

The connection part 6, to give an example, may be made up of connectors 46-48 that each comprise an electrical connector for connecting electrical wiring 62 and a connector for a probe-connection optical fiber 61, if the probe-connection optical fiber 61 and the electrical wiring 62 run along the same tube as shown in FIG. 3.

Note that when the probe-connection optical fibers 61 and the electrical wiring 62 are laid out separately, each connection part 6 is configured from an optical connector, consisting of a plug for a probe-connection optical fiber 61 and a coupler provided on the wall of the OCT main unit 1a, and an electrical connector, consisting of a plug for the electrical wiring 62 and a coupler provided on the wall of the OCT main unit 1a.

Control Unit Part

As shown in FIG. 3, the control unit part 50 (the control unit) includes an A/D converter circuit 51, a D/A converter circuit 52, a galvano mirror control circuit 53, a delay circuit 54, and an OCT control device 100.

The A/D converter circuit 51 converts an analog output signal from the detector 23 into a digital signal.

The D/A converter circuit 52 converts a digital output signal from the OCT control device 100 into an analog signal. This analog signal is inputted to the galvano mirror control circuit 53.

The galvano mirror control circuit 53 is a driver that controls the scanning unit 32 of the diagnostic probe parts 30.

The delay circuit 54 is a device for adjusting the time delay difference between electrical signals and optical signals caused by the fact that the power supply 200 and the diagnostic probe parts 30 are placed apart from one another. The delay circuit 54 delays the timing of k-clock (clock signal ck) and trigger signals in order to align them with the timing of optical system signals.

The display device 80 displays OCT images generated by the OCT control device 100. The display device 80 is, for example, composed of a liquid crystal display (LCD), an electroluminescent display (EL display), a cathode ray tube (CRT), or a plasma display panel (PDP).

The OCT control device 100 is a control device of the OCT device 1 for capturing images by controlling the scanning unit 32 in synchronicity with the laser light and for generating OCT images of the sample S from data converted from the detection signal of the detector 23. The OCT control device 100 comprises a computer, with a storage unit and a processing unit, and programs installed in the computer. The OCT control device 100 is connected electrically to a foot controller 90, a power supply 200, and an input device 9 which is made from an input/output unit.

As shown in FIG. 3, the input device 9 includes a computer instruction unit to input instructions to the actuator control part (not shown in figure) for adjusting the optical path length through moving the collimator 19a along the direction of an optical axis with the optical-path-length adjustment actuator (not shown in figure) by operating a cursor or an icon displayed on the display device 80.

Figure 6:
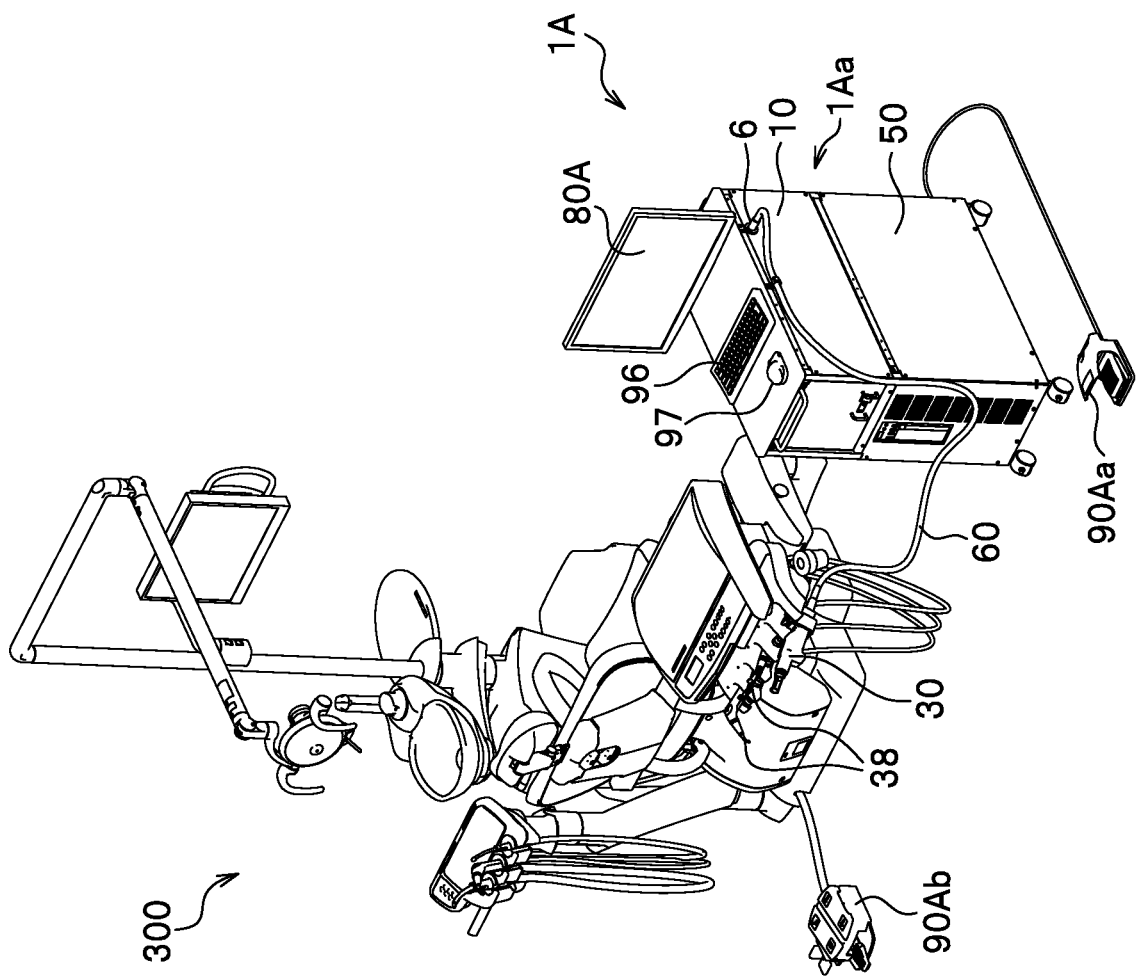
FIG. 6 is a perspective view illustrating a first modification of an OCT device according to an embodiment of the present invention where the OCT device is used by a single odonto-therapy unit.

The computer instruction unit comprises, for example, keyboard switches that are arranged on a keyboard 96 used for operating a computer (see FIG. 6) and a mouse 97 (see FIG. 6). The keyboard switches compose a control device and consists of push switches on the keyboard 96. The mouse 97 is an operating device for operating a cursor or an icon that is shown on the screen of the display device 80 and that is used to adjust the optical path length by using the forward and reverse motion of an optical-path-length adjustment actuator (not shown in figure).

Action

Next, the actions of an OCT device (the OCT device 1) according to one embodiment of the present invention is explained.

As shown in FIG. 1, the examination room R is arranged with a plurality of odonto-therapy units 300 and an OCT main unit 1a. The odonto-therapy units 300 are each arranged with a diagnostic probe part 30.

As shown in FIG. 3, the diagnostic probe parts 30A-30C connect to the OCT main body 1a by having the corresponding connector plugs 36, 36, 36 of the probe-connection optical fibers 61 and the electrical wiring 62 connect to the respective connectors 46, 47, 48 on the OCT main unit 1a. The connection between the connectors 46-48 and the connector plugs 36, 36, 36 are set in a locked state using the receptacles 37. Each of the diagnostic probe parts 30A-30C has the electrical wiring 62 connected to one of the connectors 46-48 on the side of the OCT main unit 1a using a connector plug 36.

In this way, the diagnostic probe part 30A, 30B, or 30C, the display device 80, and the foot controller 90 that are arranged on each of the odonto-therapy units 300 are connected to the OCT main unit 1a by connecting the connector plug 36 to one of the connectors 46-48.

This means that, in order to use the diagnostic probe parts 30 that are arranged across a plurality of odonto-therapy units 300, it only takes the probe-connection optical fibers 61 to be connected to the connectors 46-48 on the OCT main unit 1a. Since there is no need to move the OCT main unit 1a every time it gets used, the amount of preparation required may be cut down.

Also, the shared use of a single OCT main unit 1a by a plurality of diagnostic probe parts 30 arranged individually on each of the odonto-therapy units 300 is possible and has the following benefits. One is that space saving can be achieved by the reduction in the area occupied by the OCT main unit 1a. Second is that cost reduction can be achieved by the amount of purchase that can be saved through shared use.

Practitioners may, when using the diagnostic probe parts 30, select to use one of the diagnostic probe parts 30A-30C arranged individually on the three odonto-therapy units 300 as shown in FIG. 1. For example, to use the diagnostic probe part 30B shown in FIG. 4, the usage input unit 94 for the diagnostic probe part 30B must be turned on. By doing so, the diagnostic probe part 30B becomes connected to the OCT main unit 1a by a probe-connection optical fiber 61 and the electric wiring 62, thus enabling the use of the diagnostic probe part 30B.

Note that, as shown in FIG. 4, when the diagnostic probe part 30B is in a usable state, the laser light from the fiber collimator 45 is directed only to the diagnostic probe part 30B. Thus, the other diagnostics probe parts 30A and 30C cannot be used. In short, of the three diagnostic probe parts 30A-30C, only the one that is selected by the usage determination unit 25 is in a usable state.

Next, when the operation knob 90a of the foot controller 90 shown in FIG. 2 is stepped on, imaging of the sample S using the diagnostic probe part 30B begins.

This way, by arranging each odonto-therapy unit 300 with a foot controller 90 that is connected to the OCT main unit 1a, practitioners who use an odonto-therapy unit 300 can operate the OCT device 1 via a foot controller 90 while looking at the display device 80 and working with both hands to carry out a treatment. Due to this excellent switch operability, the process of taking sample S images can be improved.

The tomographic image of the sample S that is taken by the diagnostic probe part 30B is displayed on the display device 80 (see FIG. 1). Stepping on the operation knob 90b stops the imaging of the sample S. The taken image is saved by stepping on the operation knob 90c.

The use of one of the other two diagnostic probe parts 30A, 30C becomes possible when, upon turning on the usage input unit of a particular diagnostic probe part 30 that is either the diagnostic probe part 30A or 30C, the usage determination unit 25 determines that the particular diagnostic probe part 30 is in a usable state and switching occurs to enable its use.

This way, the odonto-therapy units 300, the OCT main unit 1a, or the diagnostic probe parts 30A-30C may, by operating the usage input units 93-95, get to transmit the laser light from the light source 11 to the diagnostic probe part 30 that needs to become operable.

As shown in FIG. 3, this invention is an OCT device 1 that splits laser light emitted from a light source 11 into measurement light, which is irradiated onto a sample S (a diagnosed object), and reference light, which is irradiated onto a reference mirror 21, and generates an OCT image by analyzing the interference light formed from combining scattered measurement light that is reflected from the sample S and reflected reference light that is reflected from the reference mirror 21. The device comprises one or more diagnostic probe parts 30 (probes) that are used to irradiate a sample S with the measurement light and collect the scattered measurement light reflected from the sample S, one or more probe-connection optical fibers 61 that are used for transmitting the measurement light and the scattered measurement light to and from the one or more diagnostic probe parts 30, and an optical distributor 4 that directs laser light emitted from the light source 11 to the diagnostic probe parts 30A, 30B, 30C.

This way, even when the number of diagnostic probe parts 30 is increased so that there are diagnostic probe parts 30A, 30B, 30C, laser light from the light source 11 may be directed to the diagnostic probe parts 30A, 30B, 30C by using the optical distributor 4. Since an OCT main unit 1a can make any one of the diagnostic probe parts 30 operable, it is possible for a single OCT main unit 1a to accommodate a plurality of the diagnostic probe parts 30.

Further, as shown in FIG. 1, it is preferable for the diagnostic probe part 30 (probe) to include a probe-connection optical fiber 61 that transmits the measurement light and the scattered measurement light, and for the probe-connection optical fiber 61 to detachably connect to the OCT main unit 1a.

By connecting a probe-connection optical fiber 61 to the OCT main unit 1a in a detachable manner, when a plurality of the probe-connection optical fibers 61 need to be connected to a single OCT main unit 1a, the heavy OCT main unit 1a does not have to be moved. Making the probe-connection optical fibers 61 detachable from the OCT main unit 1a means that the use of a diagnostic probe part 30 merely involves connecting the probe-connection optical fiber 61 thereof to the OCT main unit 1a and detaching the probe-connection optical fiber 61 when not in use. This makes the wiring of the probe-connection optical fibers 61 easy and convenient. The simplification of both the preparatory and clearing up processes for taking images of the sample S (the diagnosed object) leads to the saving of time.

Further, as shown in FIGS. 5A, 5B, it is preferable for the reflector of an optical distributor 4 to have either a reflecting mirror 4a (a reflector unit) or a prism 4e (a reflector unit) for reflecting laser light and an actuator 4d for switching between a state where the reflecting mirror 4a or the prism 4e reflects laser light and a state where the laser light is not received.

By having the actuator 4d switch the state of the reflecting mirror 4a (a reflector unit) or the prism 4e (a reflector unit) between a state where laser light gets reflected and a state where laser light is not received, the optical distributor 4 is capable of reflecting laser light from the light source 11 to the fiber collimator 49 of the desired diagnostic probe part 30. Because the reflectors 41-43 are each capable of reflecting laser light emitted from a single light source 11 to the respective diagnostic probe parts 30A-30C, the OCT device 1 is capable of effectively handling a plurality of the diagnostic probe parts 30 with just one OCT main unit 1a.

Further, as shown in FIG. 3, it is preferable for the OCT main unit 1a to include a delay circuit 54.

By having the delay circuit 54, the OCT main unit 1a is able to adjust the difference in time delays between the electrical signals and optical signals caused by the fact that the power supply 200 and the diagnostic probe parts 30 are arranged at a distance from one another. In short, by delaying the timings of k-clock (clock signal ck) and trigger signals, the delay circuit 54 is able to align them with the timing for taking in signals from the optical system.

First Modification

The present invention is not limited to the abovementioned embodiment, and may be remodeled and altered in various ways within the scope of the technical ideas of the present invention. The present invention indubitably extends to such remodeled and altered inventions. Components that have been described before are denoted by the same reference numerals, and descriptions thereof are omitted.

FIG. 6 is a perspective view illustrating the first modification of an OCT device according to an embodiment of the present invention, where the OCT device is used by a single odonto-therapy unit.

To describe the previous embodiment, an example was provided for a case where there were three odonto-therapy units 300 in an examination room R, with each odontotherapy unit 300 arranged with a diagnostic probe part 30, as shown in FIG. 1. The number of odonto-therapy units 300 and the number of diagnostic probe parts 30 may, however, be changed appropriately.

For example, as shown in FIG. 6, there need only be one odonto-therapy unit 300 and one diagnostic probe part 30, as long as the end of the cable 60 of the diagnostic probe part 30 is detachably connected to the connection part 6 of the OCT main unit 1Aa.

Further, as shown in FIG. 6, the input device 9 can be a set of keyboard switches or a pointing device such as a mouse 97 as shown in FIG. 6.

Yet further, a single odonto-therapy unit 300 can be arranged with a foot controller 90Aa, which serves as a foot-operated switch for the diagnostic probe part 30, and a foot controller 90Ab, which serves as a foot-operated switch for another handpiece 38.

Yet further, the display device 80A can be a monitor for a PC (not shown in figure).

Second Modification

Figure 7:
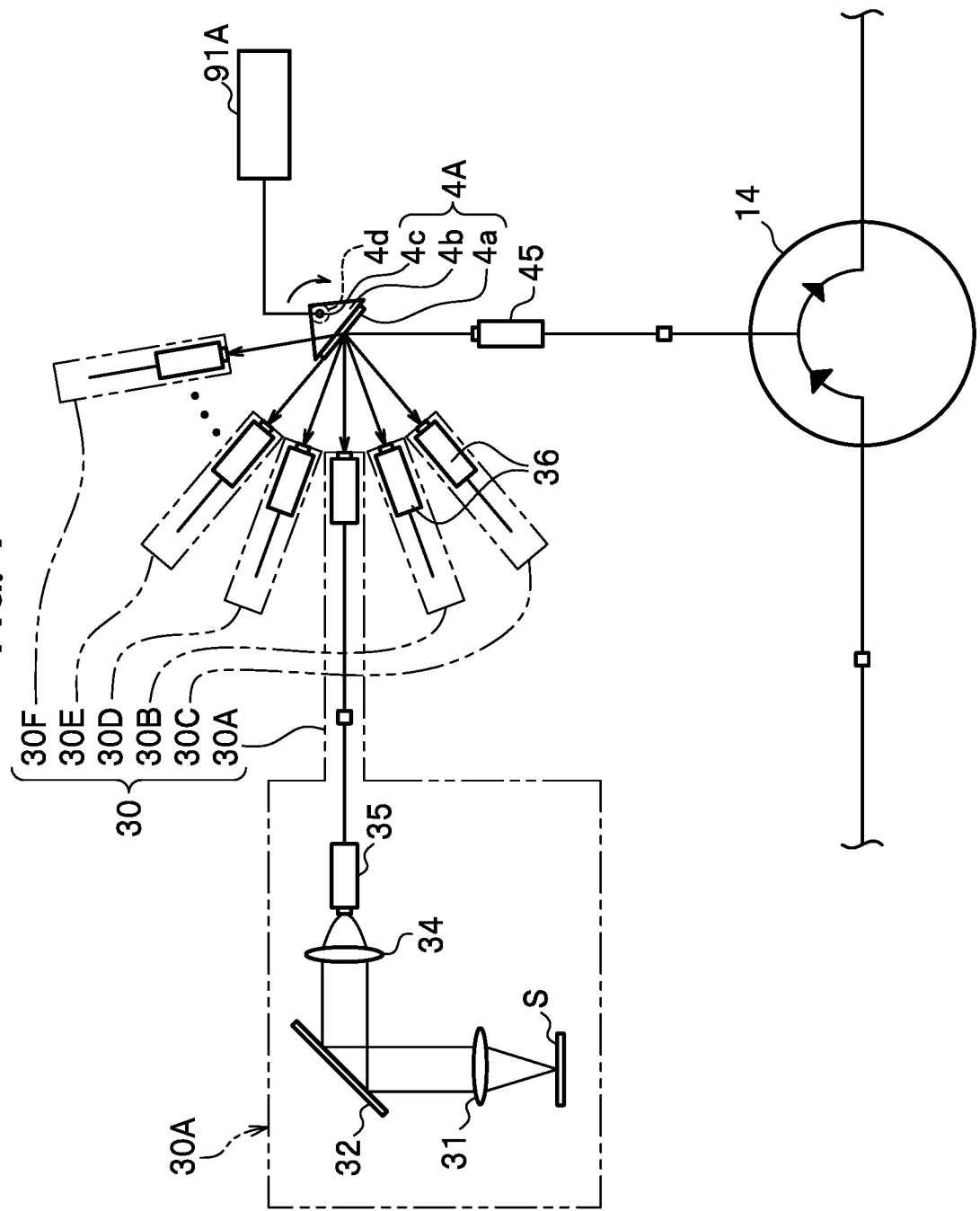
FIG. 7 is a block diagram illustrating an optical distributor for a second modification of an OCT device according to an embodiment of the present invention.

FIG. 7 is a block diagram illustrating an optical distributor for a second modification of an OCT device according to an embodiment of the present invention.

The previous embodiment was described using an example where the optical distributor 4 comprised three reflectors 41-43 as shown in FIG. 4, but the present invention is not limited to this case. As shown in FIG. 7, an optical distributor 4A configured from a single reflector may reflect laser light from the light source 11 (see FIG. 3) to a plurality of the diagnostic probe parts 30.

The optical distributor 4A of the second modification is capable of reflecting laser light from the fiber collimator 45 to the connector plugs 36 of the diagnostic probe parts 30, namely the diagnostic probe parts 30A-30F, by having the connector plugs 36 arranged around the one reflector. This way, it is possible to transmit laser light to a plurality of the diagnostic probe parts 30A-30F with a single reflector.

In this case, the optical distributor 4A comprises a reflecting mirror 4a that reflects laser light from the fiber collimator 45, a mirror mount 4b onto which the reflecting mirror 4a is attached, a pivot 4c of the mirror mount 4b, and an actuator 4d that rotationally moves the direction of reflection of the reflecting mirror 4a to the desired diagnostic probe part 30 when the usage switching unit 91 is operated to enable the use thereof.

By using this configuration, it becomes possible to send laser light to a plurality of the diagnostic probe parts 30 with an optical distributor 4A configured from a single reflector.

Third Modification

In the previous embodiment, an example of an optical distributor 4 was given, as shown in FIGS. 5A, 5B, where the reflector was configured such that the pivot 4c was rotationally driven by the actuator 4d to change the angle of the reflector unit (either a reflecting mirror 4a or prism 4e), but the present invention is not limited to this case. In other words, it is sufficient for the actuator 4d of the reflector to be capable of changing the angle of the reflector unit by rotating the pivot 4c that is fixed to the mirror mount 4b in the directions shown by the arrows a, b.

For example, the actuator 4d can be interposed with a linkage, slider mechanism, gear mechanism, solenoid, piston-cylinder mechanism, and so on to move the position of the reflector unit so that switching can occur between a state where laser light is received by the reflector unit and a state where laser light is not.

Fourth Modification

Figure 8:
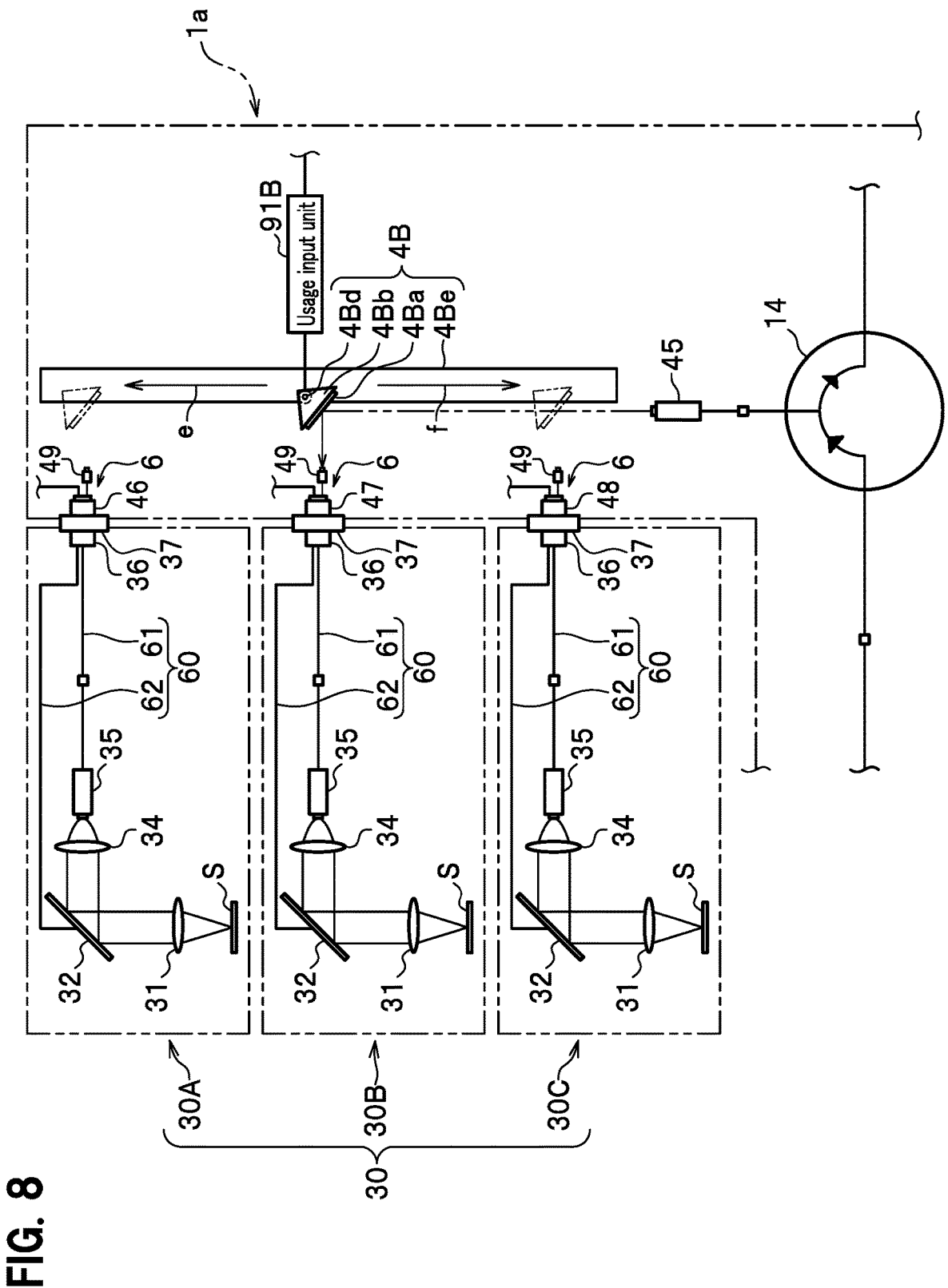
FIG. 8 is a block diagram illustrating an optical distributor for a fourth modification of an OCT device according to an embodiment of the present invention.

FIG. 8 is a block diagram illustrating an optical distributor for a fourth modification of an OCT device according to an embodiment of the present invention.

As shown in FIG. 8, the reflector of the optical distributor 4B not only switches between a state where it receives laser light and a state where it does not (such as by rotation and advance/retreat motion), but also substitutes a plurality of reflectors (such as the reflectors 41-43 of FIG. 4) for transmitting the measurement light to a specific diagnostic probe part 30 by moving the mirror mount 4Bb.

In this case, the reflector of the optical distributor 4B is configured from a reflector support unit 4Bb (which holds a reflector unit 4Ba), an electric actuator 4Bd for moving the reflector support unit 4Bb back and forth (a slide movement in the arrowed directions e, f), and a rail part 4Be, for guiding the movement of the reflector support unit 4Bb.

The actuator 4Bd is configured to move the reflector support unit 4Bb to positions along the rail part 4Be that correspond to the fiber collimators 49 of the diagnostic probe parts 30A-30C, based on the switch input signal from the usage switching unit 91B.

The rail part 4Be is arranged so that it runs in parallel with a line joining the positions of the fiber collimators 49 of the diagnostic probe parts 30A-30C.

By structuring the optical distributor 4B around a single reflector unit 4Ba in this way, the configuration of the entire OCT device can be simplified and made compact.

Note that, in this case, the optical distributor 4B can be in the form of a linear motor where the single reflector support unit 4Bb holding the reflector unit 4Ba is configured from a primary member with an armature winding and a secondary member with a permanent magnet that can move relatively to one another.

Fifth Modification

Figure 9:
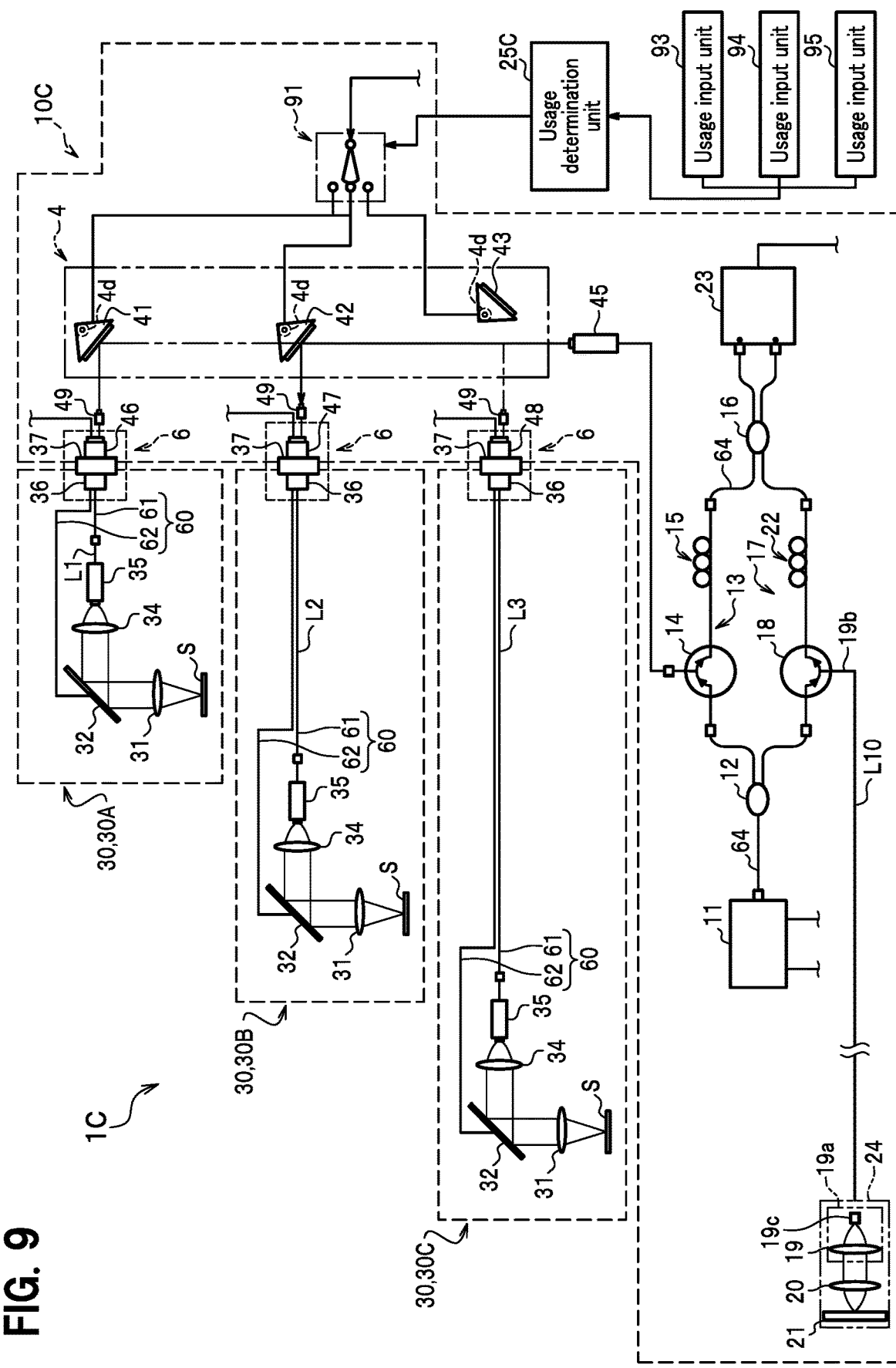
FIG. 9 is a block diagram illustrating an optical distributor for a fifth modification of an OCT device according to an embodiment of the present invention.

FIG. 9 is a block diagram illustrating an optical distributor for a fifth modification of an OCT device according to an embodiment of the present invention.

As shown in FIG. 9, the OCT main unit 1a of the present invention should preferably comprise an optical distributor 4 that is arranged between the measurement-light-side circulator 14 and the diagnostic probe parts 30A, 30B, 30C (probes), a usage switching unit 91 (an optical distribution control unit, a switching unit) for switching the optical distributor 4 based on the usage determination unit 25C that determines the use of a diagnostic probe part 30 out of a plurality of diagnostic probe parts 30, and a reference-light-side optical fiber 19b for transmitting the reference light. Moreover, the reference-light-side optical fiber 19b and the probe-connection optical fibers 61 should preferably be equal in length.

Having the optical distributor 4 arranged in this way means that when a plurality of the diagnostic probe parts 30 are connected to the optical unit part 10C, because the distance between the OCT main unit 1a and each of the diagnostic probe parts 30 differs, it is necessary to make the fiber lengths on the measurement light side (lengths L1, L2, L3 of the probe-connection optical fibers 61) equal to the fiber length on the reference light side (length L10 of the reference-light-side optical fiber 19b).

One method to achieve this, for example, is to align the fiber lengths of the diagnostic probe parts 30 (lengths L1, L2, L3 of the probe-connection optical fibers 61) with the length L3, the length of the probe-connection optical fiber 61 for a diagnostic probe part 30 with the longest distance between the corresponding fiber collimator 35 and the measurement-light-side circulator 14 of the optical unit part 10. The lengths L1, L2, L3 of the probe-connection optical fibers 61 are aligned to, say, 10 m.

In that case, the reference-light-side fiber length is set to the same length as the length to which all the measurement-light-side optical fibers have been aligned.

By having such a configuration, it becomes possible to align the fiber lengths on the measurement light side (optical path lengths) with the fiber length on the reference light side (optical path length). Further, by making the length L10 of the reference-light-side optical fiber 19b and the lengths L1, L2, L3 of the probe-connection optical fibers 61 that correspond to the diagnostic probe parts 30A, 30B, 30C the same, images of the sample S with the same degree of clarity may be achieved with any of the diagnostic probe parts 30A, 30B, 30C.

Further yet, by possessing a usage switching unit 91 that switches the optical distributor 4 based on the usage determination unit 25C that determines the use of a diagnostic probe part 30 out of a plurality of diagnostic probe parts 30A, 30B, 30C, the OCT device 1C can automatically switch the optical distributor 4 according to the diagnostic probe part 30 to be used.

Sixth Modification

Figure 10:
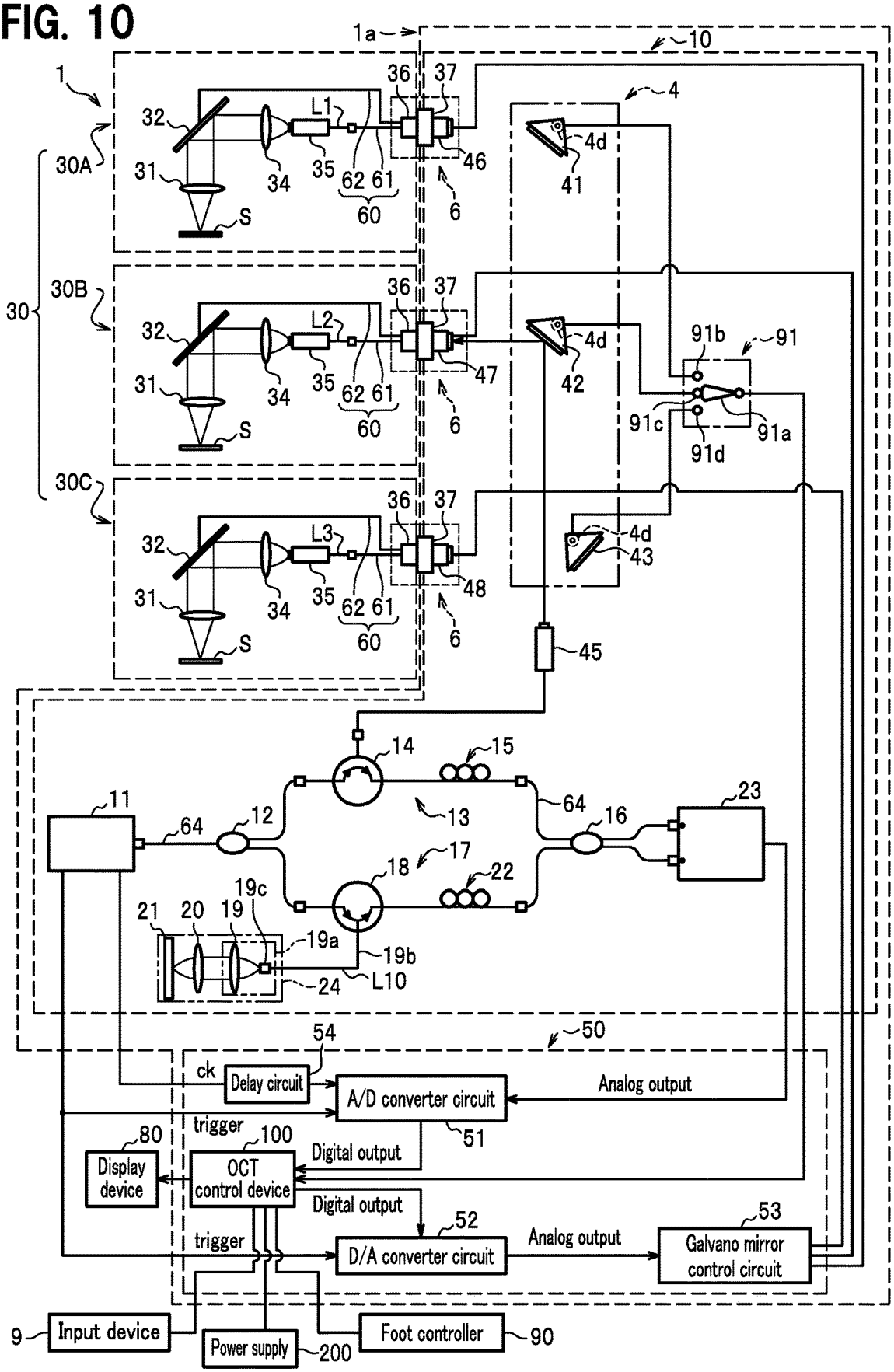
FIG. 10 is a block diagram illustrating an optical distributor for a sixth modification of an OCT device according to an embodiment of the present invention.

FIG. 10 is a block diagram illustrating an optical distributor for a sixth modification of an OCT device according to an embodiment of the present invention.

As shown in FIG. 10, the OCT main unit 1a should preferably comprise an optical distributor 4 arranged between the measurement-light-side circulator 14 and the diagnostic probe parts 30A, 30B, 30C (probes), a selection switch 91 for switching the optical distributor 4 for using a particular diagnostic probe part 30 out of a plurality of the diagnostic probe parts 30, and a reference-light-side optical fiber 19b for transmitting reference light. Moreover, the reference-light-side fiber 19b and each of the probe-connecting optical fibers 61 should preferably be equal in length.

Even when a selection switch 91, such as a rotary switch or selector switch, is used to manually switch an optical distributor 4 in this way, clear images may be acquired by making the length L10 of the reference-light-side optical fiber 19b and the lengths L1, L2, L3 of the probe-connection optical fibers 61 the same, as in the previous case where a usage switching unit 91 (an optical distribution control unit, a switching unit) is used.

Seventh Modification

Figure 11:
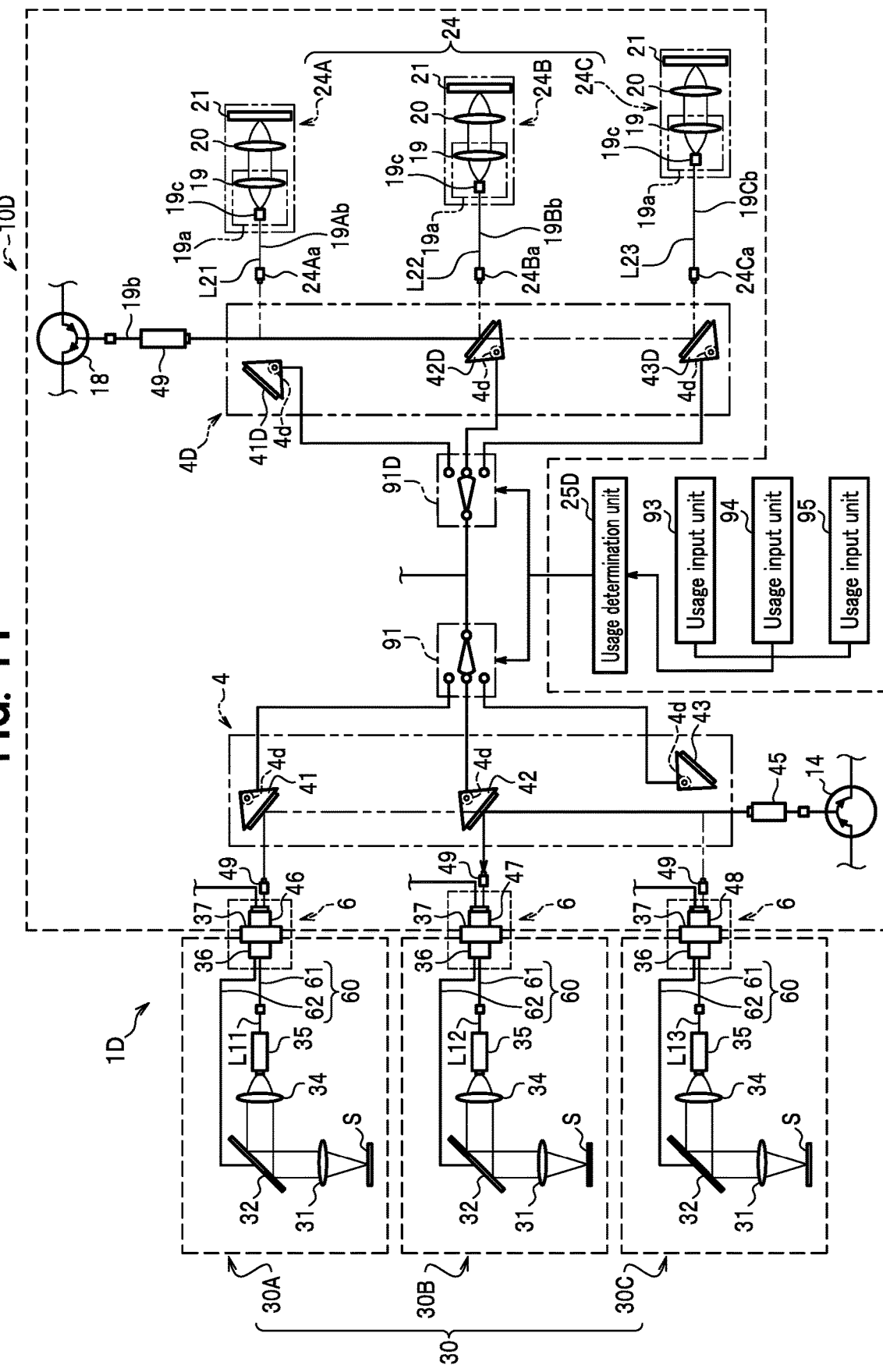
FIG. 11 is a block diagram illustrating optical distributors for a seventh modification of an OCT device according to an embodiment of the present invention.

FIG. 11 is a block diagram illustrating optical distributors for a seventh modification of an OCT device according to an embodiment of the present invention.

As shown in FIG. 11, the OCT main unit 1a of the present invention's OCT device 1D should preferably include an optical distributor 4 that is disposed between the measurement-light-side circulator 14 and the diagnostic probe parts 30 (probes), an optical distributor 4D that is disposed between the reference-light-side circulator 18 and the optical-path-length alteration unit 24 (optical-path-length setting unit), usage switching units 91, 91D for switching the pair of optical distributors 4, 4D based on the usage determination unit 25D that determines the use of a diagnostic probe part 30 out of a plurality of the diagnostic probe parts 30, and reference-light-side optical fibers 19Ab, 19Bb, 19Cb for transmitting the reference light. Moreover, it is preferable that each of the probe-connection optical fibers 61 form at least one pair of optical fibers of the same length with the reference-light side optical fibers 19Ab, 19Bb, 19Cb, and that the usage switching units 91, 91D switch the pair of optical distributors 4, 4D so that light is directed into a pair of optical fibers with the same length based on the usage determination unit 25D.

In this case, the OCT device 1D is arranged with the optical distributor 4 on the measurement light side and the optical distributor 4D on the reference light side. The reference-light-side optical distributor 4D is made up of three reflectors 41D, 42D, 43D to align with the number of diagnostic probe parts 30 and with the number of reflectors that make up the measurement-light-side optical distributor 4. There are also three optical-path-length alteration units 24, namely the optical-path-length alteration units 24A, 24B, 24C to align with the three reflectors 41D, 42D, 43D.

The usage determination unit 25D is a device that determines which of the three diagnostic probe parts 30A, 30B, 30C is in use via sensors (the usage input units 93-95).

In the OCT device 1D, the length L11 of the probe-connection optical fiber 61 measured from the fiber collimator 35 of the diagnostic probe part 30A to the corresponding fiber collimator 49 is, say, 6 m. The length L12 of the probe-connection optical fiber 61 measured from the fiber collimator 35 of the diagnostic probe part 30B to the corresponding fiber collimator 49 is, say, 8 m. The length L13 of the probe-connection optical fiber 61 from the fiber collimator 35 of the diagnostic probe part 30C to the corresponding fiber collimator 49 is, say, 10 m.

The length L21 of the reference-light-side optical fiber 19Ab measured from the connector 19c of the optical-path-length alteration unit 24A to the fiber collimator 24Aa is 6 m, which is equal to the probe-connection optical fiber 61 for the corresponding diagnostic probe part 30A.

The length L22 of the reference-light-side optical fiber 19Bb measured from the connector 19c of the optical-path-length alteration unit 24B to the fiber collimator 24Ba is 8 m, which is equal to the probe-connection optical fiber 61 for the corresponding diagnostic probe part 30B.

The length L23 of the reference-light-side optical fiber 19Cb measured from the connector 19c of the optical-path-length alteration unit 24C to the fiber collimator 24Ca is 10 m, which is equal to the probe-connection optical fiber 61 for the corresponding diagnostic probe part 30C.

By using such a configuration, even when the measurement-light-side optical distributor 4 comprises a plurality of the reflectors and when the reference-light-side optical distributor 4D comprises a plurality of the reflectors, the lengths L11, L12, L13 (optical path lengths) of the probe-connection optical fibers 61 respectively match the lengths L21, L22, L23 (optical path lengths), where L21, L22, L23 are the respective lengths of the reference-light-side optical fibers 19Ab, 19Bb, 19Cb that correspond to the diagnostic probe parts 30A, 30B, 30C respectively. So, when a diagnostic probe part 30 is selected out of the diagnostic probe parts 30A, 30B, 30C and the switching of the measurement-light-side optical distributor 4 occurs, switching of the reference-light-side optical distributor 4D also occurs so that the reference light is directed to one of the reference-lightside optical fibers 19Ab, 19Bb, or 19Cb having the same length as that of the probe-connection optical fiber 61 on the measurement-light side.

Although the seventh modification requires a pair of optical distributors 4, 4D, it does not need to have optical fibers with excess lengths. Optical fibers with lengths that are adequate considering the distance to the individual diagnostic probe parts 30A, 30B, 30C and the optical-path-length alteration units 24A, 24B, 24C can be used.

Alternatively, the OCT main unit 1a should preferably include an optical distributor 4 that is disposed between the measurement-light-side circulator 14 and the diagnostic probe parts 30 (probes), an optical distributor 4D that is disposed between the reference-light-side circulator 18 and the optical-path-length alteration units 24 (optical-path-length setting units), selection switches 91, 91D for switching the pair of optical distributors 4, 4D for using a particular diagnostic probe part 30 out of a plurality of diagnostic probe parts 30, and reference-light-side optical fibers 19Ab, 19Bb, 19Cb for transmitting the reference light. Moreover, it is preferable that each of the probe-connection optical fibers 61 form at least one pair of optical fibers of the same length with the reference-light side optical fibers 19Ab, 19Bb, 19Cb, and that the selection switch 91, 91D switch the pair of optical distributors 4, 4D so that light is directed into a pair of optical fibers with the same length.

By using such a configuration, it becomes possible for the length of the measurement-light-side optical fiber (optical path length) and the length of the reference-light-side optical fiber (optical path length) to be aligned by simply switching the optical distributors 4, 4D with the selection switches 91, 91D.

Eighth Modification

Figure 12:
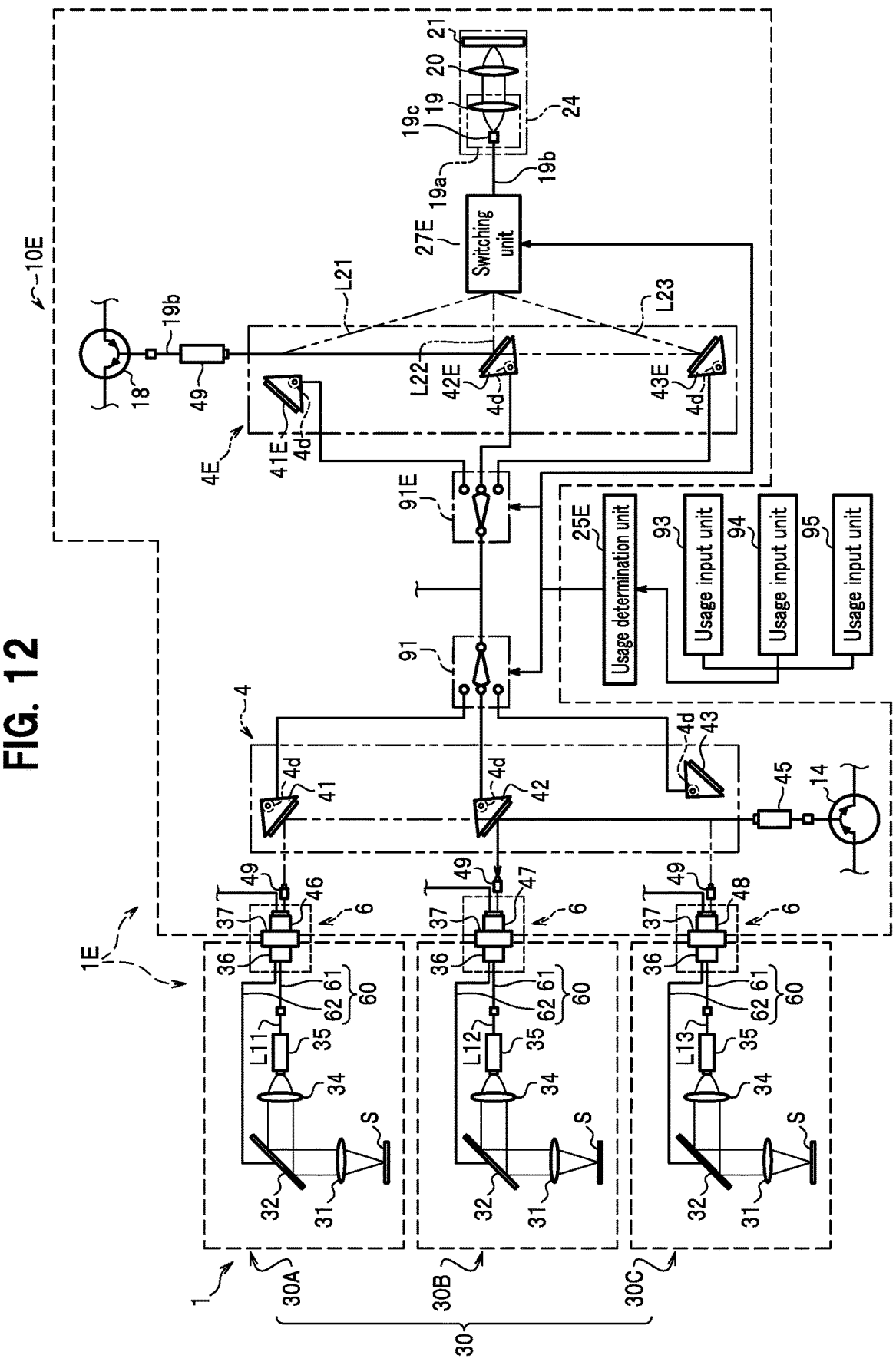
FIG. 12 is a block diagram illustrating optical distributors for an eighth modification of an OCT device according to an embodiment of the present invention.

FIG. 12 is a block diagram illustrating optical distributors for an eighth modification of an OCT device according to an embodiment of the present invention.

The seventh modification of the OCT device 1D was described with an example where the three optical-path-length alteration units 24, namely the optical-path-length alteration units 24A, 24B, 24C, were arranged in alignment with the three reflectors 41D, 42D, 43D of the reference-light side optical distributor 4D, but the present invention is not limited to this case.

By placing a switching unit 27E as shown in the OCT device 1E of FIG. 12, it is possible to configure a reference-light-side optical distributor 4E consisting of three reflectors 41E, 42E, and 43E with a single optical-path-length alteration unit 24.

In this case, the OCT device 1E may have measurement-light-side optical fiber lengths (lengths L11, L12, L13 of the probe-connection optical fibers 61), measured from the measurement-light-side circulator 14 to the fiber collimator 35 of each of the diagnostic probe parts 30A, 30B, 30C, differ or are equal to one another.

The length L21 of the reference-light-side optical fiber 19b, measured from the reference-light-side circulator 18, via the reflector 41E, to the collimator 19a of the optical-path-length alteration unit 24, is equal to the length L11 of the probe-connection optical fiber 61 for the diagnostic probe part 30A, measured from the measurement-light-side circulator 14 to the corresponding fiber collimator 35.

The length L22 of the reference-light-side optical fiber 19b, measured from the reference-light-side circulator 18, via the reflector 42E, to the collimator 19a of the optical-path-length alteration unit 24, is equal to the length L12 of the probe-connection optical fiber 61 for the diagnostic probe part 30B, measured from the measurement-light-side circulator 14 to the corresponding fiber collimator 35.

The length L23 of the reference-light-side optical fiber 19b, measured from the reference-light-side circulator 18, via the reflector 43E, to the collimator 19a of the optical-path-length alteration unit 24, is equal to the length L13 of the probe-connection optical fiber 61 for the diagnostic probe part 30C measured from the measurement-light-side circulator 14 to the corresponding fiber collimator 35.

By using such a configuration, it becomes possible to configure a reference-light-side optical distributor 4E consisting of a plurality of reflectors with a single optical-path-length alteration unit 24 by placing a switching unit 27E, thus enabling a reduction in cost.

Ninth Modification

Figure 13:
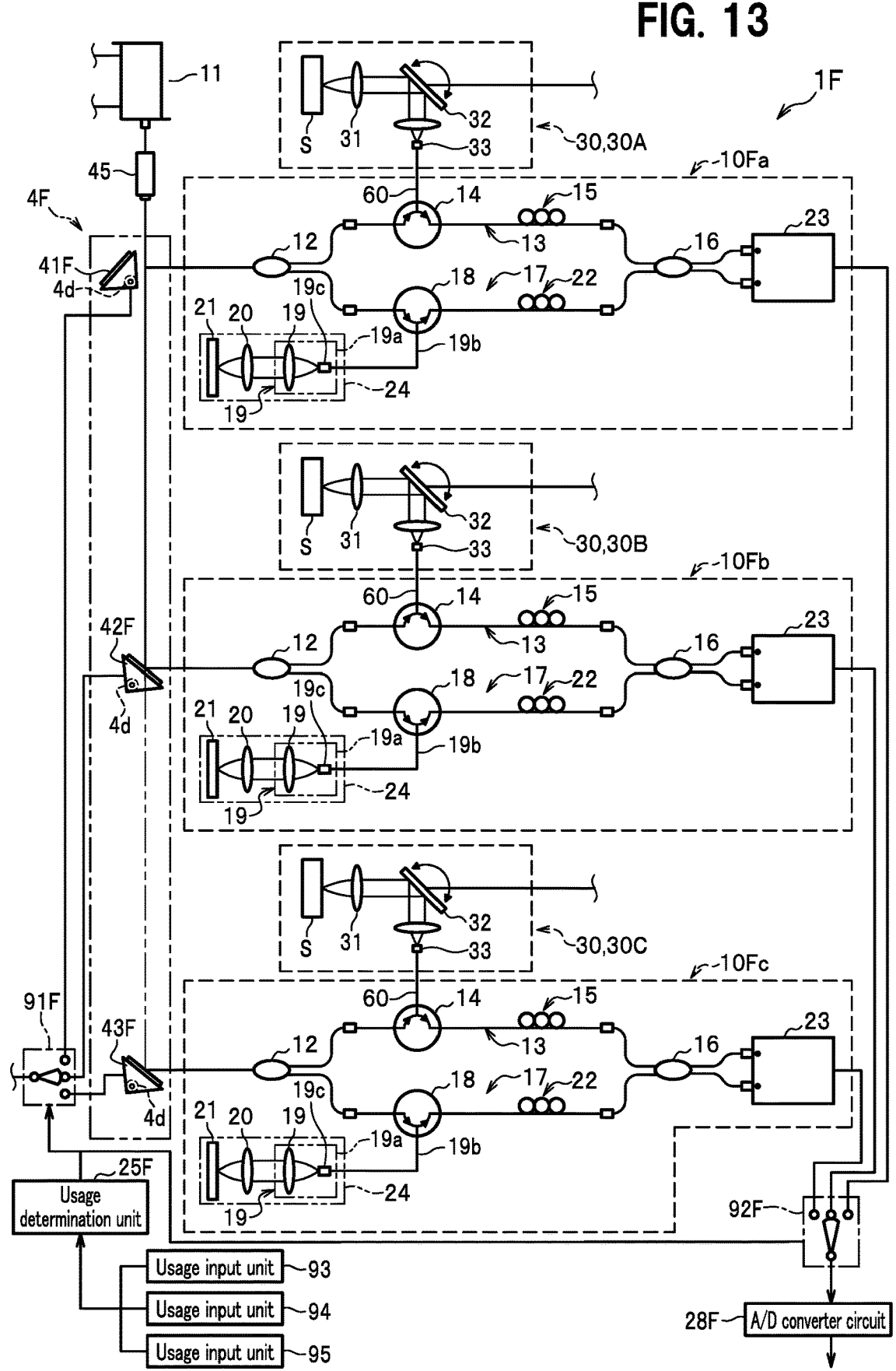
FIG. 13 is a block diagram illustrating an optical distributor for a ninth modification of an OCT device according to an embodiment of the present invention.

FIG. 13 is a block diagram illustrating an optical distributor for a ninth modification of an OCT device according to an embodiment of the present invention.

As shown in FIG. 13, the OCT main unit 1a of the present invention's OCT device 1F should preferably include an optical distributor 4F arranged between the light source 11 and couplers 12, a usage switching unit 91F for switching the optical distributor 4F, and an output switching device (a switching unit 92F) for outputting one of the outputs from a plurality of interference-light-detecting detectors 23. Moreover, the OCT main unit 1a should preferably control the usage switching unit 91F and the output switching device (the switching unit 92F) using a usage determination unit 25F, which determines the use of one of the diagnostic probe parts 30 (probes).

In this case, the OCT device 1F has three diagnostic probe parts 30A, 30B, 30C, three optical unit parts 10Fa, 10Fb, 10Fc that are arranged to correspond to the respective diagnostic probe parts 30A, 30B, 30C, and an optical distributor 4F consisting of three reflectors 41F, 42F, 43F that correspond to the three optical unit parts 10Fa, 10Fb, 10Fc respectively. The reflectors 41F, 42F, 43F are arranged in the vicinity of the light source 11.

The usage determination unit 25F is a device that determines which of the diagnostic probe parts 30A, 30B, 30C is the diagnostic probe part 30 in use.

The usage switching unit 91F is a device for switching the optical distributor 4F based on the diagnostic probe part 30 in use as determined by the usage determination unit 25F.

The output switching device (the switching unit 92F) is a device that drives the switching to one of the optical unit parts 10Fa, 10Fb, 10Fc according to the diagnostic probe part 30 in use, upon receiving a control signal from the usage determination unit 25E The switching unit 92F is connected to an A/D converter circuit 28E It is possible to make the A/D converter circuit 28F receive at its input multiple analog outputs. In the case being described, because the optical unit parts 10Fa, 10Fb, 10Fc, which exclude the light source 11, are arranged as separate units from the OCT main unit 1a, the OCT device is configured so that analog outputs from a plurality of detectors 23 are returned to the OCT main unit 1a. The switching unit 92F is provided to input one of the analog outputs to the A/D converter circuit 28F.

The optical distributor 4F and the switching unit 92F are controlled based on the usage determination unit 25F.

By using such a configuration, it becomes possible to handle cases where there is an optical distributor 4F on the illumination side and a plurality of diagnostic probe parts 30A, 30B, 30C by arranging corresponding optical unit parts 10Fa, 10Fb, 10Fc and having a switching unit 92F to switch between them.

In this case, there must be a plurality of optical unit parts 10Fa, 10Fb, 10Fc, which exclude the light source 11. However, the fiber lengths (optical path lengths) within each of the optical unit parts 10Fa, 10Fb, 10Fc need not be the same. Also, it is possible for the optical unit parts 10Fa, 10Fb, 10Fc, which exclude the light source 11, to be incorporated within a unit or be stored in a case and placed close to the unit.

In another case of the ninth modification, it is preferable for the OCT main unit 1a to possess an optical distributor 4F, which is disposed between the light source 11 and couplers 12, a usage switching unit 91F for switching the optical distributor 4F, and an output switching device (a switching unit 92F) for outputting one of the outputs from a plurality of detectors 23 that detect interference light. Moreover, the OCT main unit 1a should preferably have a master selection switch (a usage determination unit 25F) for controlling the usage switching unit 91F and the output switching device (the switching unit 92F) for using one of the diagnostic probe parts 30 (probes). The master selection switch may be configured from, say, a circuit with a rotary switch or selector switch.

With this configuration, it is possible to handle cases with an optical distributor 4F on the illumination side and a plurality of diagnostic probe parts 30 by switching between the corresponding optical unit parts 10Fa, 10Fb, 10Fc using the master selection switch (the usage determination unit 25F).

Tenth Modification

Preferably, as shown in FIGS. 9 to 13, the OCT devices 1C, 1D, 1E, 1F of the fifth to ninth modifications should have the usage determination units 25C, 25D, 25E, 25F determine input from the usage input units 93-95 provided on the odonto-therapy units 300, the OCT main unit 1a, or the diagnostic probe parts 30.

In these cases, the usage input units 93-95 may be categorized into four types.

The first type of usage input units 93-95 refers to cases where switching is carried out by determining that a diagnostic probe part 30 is held based on a signal from a priority circuit mechanism of an odonto-therapy unit 300, which uses a probe attachment/detachment detection sensor and so on to detect whether a diagnostic probe 30 is attached onto or detached from a hanger 360 of the odonto-therapy unit 300 (see FIG. 1 and FIG. 2).

The second type of usage input units 93-95 refers to cases where a hanger 360, which is separate from an instrument hanger 340 is provided somewhere on the odonto-therapy unit 300, and where the hanger 360 is equipped with a probe-detection sensor that detects whether a diagnostic probe part 30 is in use (see FIG. 1 and FIG. 2).

The third type of usage input units 93-95 refers to cases where each of the diagnostic probe parts 30 is equipped with a switch that indicates its usage status. An example of this would be to have an on-off switch on the diagnostic probe parts 30.

The fourth type of usage input units 93-95 refers to cases where the OCT main unit 1a is equipped with a switch such as a rotary switch or any other appropriate type of switch.

Upon receiving a signal from any of the usage input units 93-95 (for example, switches on the diagnostic probe parts 30) corresponding to a particular diagnostic probe part 30, the usage determination units 25C, 25D, 25E, 25F does not allow the usage switching unit 91 to carry out switching when another diagnostic probe part 30 is already in use, but will determine that usage is possible if none of the diagnostic probe parts 30 are in use. If a plurality of signals arrive from the usage input units 93-95, the first signal that is received is prioritized.

The optical distributors 4, 4D, 4E, or 4F then get switched so that light is directed to the diagnostic probe part 30 that was selected through any of the four types of usage input units 93-95. In short, the eighth modification of the present invention controls the optical distributors 4, 4D, 4E, and 4F in synchrony with signals of the usage determination units 25C-25F.

Signals from the usage determination units 25C-25F are first inputted to the OCT control device 100 or a separate control device (a usage switching unit 92). These control devices then carry out the switching by driving one or more actuators 4d of the optical distributors 4, 4D, 4E, 4F directly in some cases. In other cases, these devices may switch the usage switching unit 91 to drive one or more actuators 4d as shown in FIG. 3.

With such a configuration where the OCT devices 1C, 1D, 1E, 1F comprise the usage determination units 25C, 25D, 25E, or 25F, each of the OCT devices 1C, 1D, 1E, 1F can change its state as a whole to respond to the use of any one of a plurality of diagnostic probe parts 30.

Eleventh Modification

Further, in the present invention, it is preferable for the instrument hanger 340 of odonto-therapy units 300 to be equipped with a diagnostic probe part 30 as shown in FIGS. 1 to 3, and for the usage determination unit to determine the input from the usage input units 93-95 that form a priority circuit mechanism that detects the displacement of an instrument 400 from a hanger 360 and the placement of an instrument 400 on the hanger 360 and controls a drive circuit to drive a displaced instrument 400, with priority given to the one which has been displaced the earliest.

Preferably, each odonto-therapy unit 300 should be equipped with a display device 80 and a foot controller 90 that are individually connected to the OCT main unit 1a. Furthermore, the priority circuit mechanism should preferably switch over the display device 80 and the foot controller 90 for use with the diagnostic probe part 30 based on the displacement of an instrument 400 from a hanger 360 and/or the placement of an instrument 400 on a hanger 360.

By using such a configuration, when the odonto-therapy units 300 are each equipped with a plurality of instruments 400 (which includes a diagnostic probe part 30), the use of a priority circuit mechanism means that a special hanger 360 or a switch (the usage input units 93-95) is not required for installing a diagnostic probe part 30.

Further, when an odonto-therapy unit 300 is identified as having a diagnostic probe part 30 that is being held, the foot controller 90 and/or display device 80 (and other devices) attached to that odonto-therapy unit 300 become available for use for the operation of the OCT device 1. In other words, the display device 80 and the foot controller 90 attached to the odonto-therapy unit 300 can be made to serve both the OCT device 1 and the odonto-therapy unit 300. Not requiring a separate display device 80 nor a foot controller 90 for the OCT main unit 1a has benefits including the prevention of using the wrong foot controller 90 and cost reduction.

Other Modifications

Although the OCT main unit 1a shown in FIG. 1 is placed apart from the odonto-therapy units 300 of the examination room R, it can be placed as part of one of the odonto-therapy units 300. Alternatively, the main unit 1a can be placed in a different room to the examination room R.

Although FIG. 3 shows a case where the usage input units 93-95 are arranged as part of the OCT main unit 1a, they can be arranged on the corresponding odonto-therapy units 300, or, alternatively, arranged on the corresponding diagnostic probe parts 30A-30C.

For example, in cases where the usage input units 93-95 are arranged on the corresponding odonto-therapy units 300, they can each be in the form of an attachment/detachment switch that detects whether a diagnostic probe part 30 is attached to or detached from an instrument hanger 340, a push switch 351 arranged on a control panel 350, and so on. When the usage input units 93-95 are in the form of an attachment/detachment switch, they can be an optical switch that turns on when a diagnostic probe part 30 is detached from an instrument hanger 340, or they can be a physically activated switch that is turned off when a diagnostic probe part 30 is attached and turned on when it is detached.

In cases where these usage input units 93-95 are employed, the one out of the usage input units 93-95 that is turned on the earliest, which corresponds a particular diagnostic probe part 30, is prioritized and is made to connect electrically to the OCT main unit 1a so that only the particular diagnostic probe part 30 can be used. Once the diagnostic probe part 30 is returned to the original position on the odonto-therapy unit 300 after use, the corresponding usage input unit 93, 94, or 95 is turned off, and it once again becomes possible to use other diagnostic probe parts 30.

Further, the usage input units 93-95 may each be arranged on the display device 80 of the corresponding odonto-therapy unit 300, and can be in the form of, say, a touch switch or push switch.

Further yet, the usage input units 93-95 may each be arranged on the corresponding diagnostic probe part 30, and can be in the form of, say, a push button switch disposed on the housing 3 of the diagnostic probe part 30.

Further yet, in the embodiment described earlier, an example of an OCT device 1 was given where a straight-type diagnostic probe part 30, suitable when the sample S is a front tooth (an incisor), was used, but the present invention is not limited to this. The diagnostic probe part 30 can have its nozzle replaced with an angular-type nozzle when the sample S is a molar.

Obviously, numerous modifications and variations of the present invention are possible in light of the above teachings. It is therefore to be understood that within the scope of the appended claims, the invention may be practiced otherwise than as specifically described herein.

What is claimed is:

1. An optical coherence tomography imaging device (referred to as an OCT device), the OCT device comprising:
   an OCT main unit including: a light source configured to emit laser light, an optical splitter configured to split the laser light into measurement light for an object and reference light, and one or more reference mirrors configured to reflect the reference light;
   probes configured to irradiate the object with the measurement light and collect scattered measurement light that is reflected from the object; and
   probe-connection optical fibers configured to transmit the measurement light and the scattered measurement light to and from the probes,
   wherein the OCT main unit further includes an optical distributor arranged on a path of the measurement light between the optical splitter and the probes, the optical distributor comprising one or more reflectors configured to move to switch between the probes,
   wherein the one or more reflectors are configured to reflect the measurement light to one of the probes,
   wherein the scattered measurement light and reflected reference light are combined into interference light for analysis to generate an OCT image,
   wherein the OCT main unit further includes a usage switching unit configured to switch the optical distributor based on a usage determination unit that determines which one of the probes is to be used,
   wherein the usage determination unit determines input from one or more usage input units, the one or more usage input units being provided on one or more odonto-therapy units, the OCT main unit, or the probes,
   wherein an instrument hanger of each of the one or more odonto-therapy units is equipped with a probe, and
   wherein the usage determination unit determines input from the one or more usage input units that form a priority circuit mechanism that detects a displacement of an instrument from a hanger and a placement of an instrument on a hanger and controls a driving circuit to drive an instrument with priority given to the instrument that is displaced the earliest.

2. The OCT device according to claim 1, wherein each of the one or more reflectors comprises:
   a prism or mirror configured to reflect the laser light; and
   an actuator configured to switch the prism or mirror between a state for reflecting the laser light and a state where the prism or mirror does not receive the laser light.

3. The OCT device according to claim 2, wherein the OCT main unit further comprises:
   a reference-light optical fiber configured to transmit the reference light,
   wherein the reference-light optical fiber and each of the probe-connection optical fibers are equal in length.

4. The OCT device according to claim 3,
   wherein each of the one or more odonto-therapy units possesses, in addition to a probe, a display device that is individually connected to the OCT main unit and a foot controller that is individually connected to the OCT main unit,
   wherein the priority circuit mechanism switches over the display device and the foot controller for use with the probe based on the displacement of an instrument from a hanger and/or the placement of an instrument on a hanger.

5. The OCT device according to claim 1, wherein the one or more reflectors are configured to rotate between a position on the path of the measurement light and a position out of the path.

6. The OCT device according to claim 1, wherein the one or more reflectors comprise a reflector configured to rotate between rotational positions corresponding to the probes respectively.

7. The OCT device according to claim 1, wherein the one or more reflectors comprise a reflector configured to translationally move between translational positions corresponding to the probes respectively.

\* \* \* \* \*